United States Patent
Lieber et al.

(10) Patent No.: US 9,535,063 B2
(45) Date of Patent: *Jan. 3, 2017

(54) HIGH-SENSITIVITY NANOSCALE WIRE SENSORS

(71) Applicant: President and Fellows of Harvard College, Cambridge, MA (US)

(72) Inventors: Charles M. Lieber, Lexington, MA (US); Xuan Gao, Cambridge, MA (US); Gengfeng Zheng, Dorchester, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 36 days.

This patent is subject to a terminal disclaimer.

(21) Appl. No.: 14/030,170

(22) Filed: Sep. 18, 2013

(65) Prior Publication Data

US 2014/0080139 A1 Mar. 20, 2014

Related U.S. Application Data

(63) Continuation of application No. 12/312,740, filed as application No. PCT/US2007/024126 on Nov. 19, 2007, now Pat. No. 8,575,663.
(Continued)

(51) Int. Cl.
*G01N 27/414* (2006.01)
*G01N 33/552* (2006.01)
(Continued)

(52) U.S. Cl.
CPC ............. *G01N 33/552* (2013.01); *B82Y 15/00* (2013.01); *B82Y 30/00* (2013.01); *G01N 27/4146* (2013.01)

(58) Field of Classification Search
None
See application file for complete search history.

(56) References Cited

U.S. PATENT DOCUMENTS 905,586 A 12/1908 Rigney
3,873,359 A 3/1975 Lando
(Continued)

FOREIGN PATENT DOCUMENTS

CN 1110786 10/1995
EP 0622439 11/1994
(Continued)

OTHER PUBLICATIONS

Chenadii Korotcenkov, "Chemical Sensors Simulation and Modeling, vol. 5: Electrochemical Sensors", Momentum Press, LLC, New York, 2013, the link to the textbook: https://books.google.com/books?id=nchV4E9H8UUC&pg=PT382&lpg=PT382&dq=debye+screening+length+and+chemistry&source=bl&ots=-MbwSkYmly&sig=MmTAGoeCMM9iXyrhnND-WpBRdLA&hl=en&sa=X&ved=0CGIQ6A.*
(Continued)

*Primary Examiner* — Daniel Whalen
(74) *Attorney, Agent, or Firm* — Wolf, Greenfield & Sacks, P.C.

(57) ABSTRACT

One aspect of the invention provides a nanoscale wire that has improved sensitivity, for example, as the carrier concentration in the wire is controlled by an external gate voltage. In one set of embodiments, the nanoscale wire has a Debye screening length that is greater than the average cross-sectional dimension of the nanoscale wire when the nanoscale wire is exposed to a solution suspected of containing an analyte. In certain instances, the Debye screening length associated with the carriers inside nanoscale wire may be adjusted by adjusting the voltage, for example, a gate voltage applied to an FET structure. In some cases, the
(Continued)

nanoscale wire can be operated under conditions where the carriers in the nanoscale wire are depleted and the nanoscale wire has a conductance that is not linearly proportional to the voltage applied to the nanoscale wire sensor device, for example, via a gate electrode.

20 Claims, 8 Drawing Sheets

Related U.S. Application Data

(60) Provisional application No. 60/860,586, filed on Nov. 22, 2006.

(51) Int. Cl.
  *B82Y 15/00* (2011.01)
  *B82Y 30/00* (2011.01)

(56) References Cited

U.S. PATENT DOCUMENTS

| | | |
|---|---|---|
| 3,873,360 A | 3/1975 | Lando |
| 3,900,614 A | 8/1975 | Lando |
| 4,341,009 A | 7/1982 | Bartholomew et al. |
| 4,673,474 A | 6/1987 | Ogawa |
| 4,939,556 A | 7/1990 | Eguchi et al. |
| 5,023,139 A | 6/1991 | Birnboim et al. |
| 5,089,545 A | 2/1992 | Pol |
| 5,252,835 A | 10/1993 | Lieber et al. |
| 5,274,602 A | 12/1993 | Glenn |
| 5,332,910 A | 7/1994 | Haraguchi et al. |
| 5,453,970 A | 9/1995 | Rust et al. |
| 5,475,341 A | 12/1995 | Reed |
| 5,512,131 A | 4/1996 | Kumar et al. |
| 5,524,092 A | 6/1996 | Park |
| 5,537,075 A | 7/1996 | Miyazaki |
| 5,539,214 A | 7/1996 | Lynch et al. |
| 5,581,091 A | 12/1996 | Moskovits et al. |
| 5,589,692 A | 12/1996 | Reed |
| 5,607,876 A | 3/1997 | Biegelsen et al. |
| 5,620,850 A | 4/1997 | Bamdad et al. |
| 5,640,343 A | 6/1997 | Gallagher et al. |
| 5,672,480 A | 9/1997 | Dowell et al. |
| 5,726,524 A | 3/1998 | Debe |
| 5,739,057 A | 4/1998 | Tiwari et al. |
| 5,747,180 A | 5/1998 | Miller et al. |
| 5,751,156 A | 5/1998 | Muller et al. |
| 5,776,748 A | 7/1998 | Singhvi et al. |
| 5,824,470 A | 10/1998 | Baldeschwieler et al. |
| 5,830,538 A | 11/1998 | Gates et al. |
| 5,840,435 A | 11/1998 | Lieber et al. |
| 5,847,565 A | 12/1998 | Narayanan |
| 5,858,862 A | 1/1999 | Westwater et al. |
| 5,864,823 A | 1/1999 | Levitan |
| 5,866,434 A | 2/1999 | Massey et al. |
| 5,882,779 A | 3/1999 | Lawandy |
| 5,897,945 A | 4/1999 | Lieber et al. |
| 5,900,160 A | 5/1999 | Whitesides et al. |
| 5,903,010 A | 5/1999 | Flory et al. |
| 5,908,692 A | 6/1999 | Hamers et al. |
| 5,916,642 A | 6/1999 | Chang |
| 5,936,703 A | 8/1999 | Miyazaki et al. |
| 5,942,443 A | 8/1999 | Parce et al. |
| 5,985,173 A | 11/1999 | Gray et al. |
| 5,997,832 A | 12/1999 | Lieber et al. |
| 6,004,444 A | 12/1999 | Aksay et al. |
| 6,036,774 A | 3/2000 | Lieber et al. |
| 6,038,060 A | 3/2000 | Crowley |
| 6,060,121 A | 5/2000 | Hidber et al. |
| 6,060,724 A | 5/2000 | Flory et al. |
| 6,069,380 A | 5/2000 | Chou et al. |
| 6,123,819 A | 9/2000 | Peeters |
| 6,128,214 A | 10/2000 | Kuekes et al. |
| 6,143,184 A | 11/2000 | Martin et al. |
| 6,149,819 A | 11/2000 | Martin et al. |
| 6,159,742 A | 12/2000 | Lieber et al. |
| 6,180,239 B1 | 1/2001 | Whitesides et al. |
| 6,187,165 B1 | 2/2001 | Chien et al. |
| 6,190,634 B1 | 2/2001 | Lieber et al. |
| 6,197,515 B1 | 3/2001 | Bamdad et al. |
| 6,203,864 B1 | 3/2001 | Zhang et al. |
| 6,207,392 B1 | 3/2001 | Weiss et al. |
| 6,211,464 B1 | 4/2001 | Mochizuki et al. |
| 6,231,744 B1 | 5/2001 | Ying et al. |
| 6,248,674 B1 | 6/2001 | Kamins et al. |
| 6,256,767 B1 | 7/2001 | Kuekes et al. |
| 6,270,074 B1 | 8/2001 | Rasmussen et al. |
| 6,278,231 B1 | 8/2001 | Iwasaki et al. |
| 6,286,226 B1 | 9/2001 | Jin |
| 6,287,765 B1 | 9/2001 | Cubicciotti |
| 6,294,399 B1 | 9/2001 | Fukumi et al. |
| 6,294,450 B1 | 9/2001 | Chen et al. |
| 6,314,019 B1 | 11/2001 | Kuekes et al. |
| 6,322,713 B1 | 11/2001 | Choi et al. |
| 6,325,904 B1 | 12/2001 | Peeters |
| 6,340,822 B1 | 1/2002 | Brown et al. |
| 6,346,189 B1 | 2/2002 | Dai et al. |
| 6,355,198 B1 | 3/2002 | Kim et al. |
| 6,359,288 B1 | 3/2002 | Ying et al. |
| 6,413,802 B1 | 7/2002 | Hu et al. |
| 6,437,329 B1 | 8/2002 | Yedur et al. |
| 6,440,637 B1 | 8/2002 | Choi et al. |
| 6,451,113 B1 | 9/2002 | Givargizov |
| 6,459,095 B1 | 10/2002 | Heath et al. |
| 6,465,132 B1 | 10/2002 | Jin |
| 6,465,331 B1 | 10/2002 | Keeth et al. |
| 6,468,657 B1 | 10/2002 | Hou et al. |
| 6,468,677 B1 | 10/2002 | Benton et al. |
| 6,503,375 B1 | 1/2003 | Maydan et al. |
| 6,528,020 B1 | 3/2003 | Dai et al. |
| 6,538,367 B1 | 3/2003 | Choi et al. |
| 6,559,468 B1 | 5/2003 | Kuekes et al. |
| 6,586,095 B2 | 7/2003 | Wang et al. |
| 6,628,053 B1 | 9/2003 | Den et al. |
| 6,716,409 B2 | 4/2004 | Hafner et al. |
| 6,741,019 B1 | 5/2004 | Filas et al. |
| 6,743,408 B2 | 6/2004 | Lieber et al. |
| 6,756,025 B2 | 6/2004 | Colbert et al. |
| 6,756,795 B2 | 6/2004 | Hunt et al. |
| 6,762,056 B1 | 7/2004 | Peeters |
| 6,781,166 B2 | 8/2004 | Lieber et al. |
| 6,803,840 B2 | 10/2004 | Hunt et al. |
| 6,808,746 B1 | 10/2004 | Dai et al. |
| 6,815,706 B2 | 11/2004 | Li et al. |
| 6,822,051 B2 | 11/2004 | Harris |
| 6,846,565 B2 | 1/2005 | Korgel et al. |
| 6,846,654 B1 | 1/2005 | Blackburn et al. |
| 6,872,645 B2 | 3/2005 | Duan et al. |
| 6,882,051 B2 | 4/2005 | Majumdar et al. |
| 6,882,767 B2 | 4/2005 | Yang et al. |
| 6,900,479 B2 | 5/2005 | Lieber et al. |
| 6,902,720 B2 | 6/2005 | McGimpsey |
| 6,946,197 B2 | 9/2005 | Yadav et al. |
| 6,958,216 B2 | 10/2005 | Kelley et al. |
| 6,962,823 B2 | 11/2005 | Empedocles et al. |
| 6,963,077 B2 | 11/2005 | Lieber et al. |
| 6,974,706 B1 | 12/2005 | Melker et al. |
| 6,996,147 B2 | 2/2006 | Majumdar et al. |
| 7,048,903 B2 | 5/2006 | Colbert et al. |
| 7,073,157 B2 | 7/2006 | Lieber et al. |
| 7,129,554 B2 | 10/2006 | Lieber et al. |
| 7,172,953 B2 | 2/2007 | Lieber et al. |
| 7,211,464 B2 | 5/2007 | Lieber et al. |
| 7,254,151 B2 | 8/2007 | Lieber et al. |
| 7,256,466 B2 | 8/2007 | Lieber et al. |
| 7,274,208 B2 | 9/2007 | Lieber et al. |
| 7,301,199 B2 | 11/2007 | Lieber et al. |
| 7,303,875 B1 | 12/2007 | Bock et al. |
| 7,335,908 B2 | 2/2008 | Samuelson et al. |
| 7,351,313 B2 | 4/2008 | Hasegawa et al. |
| 7,385,267 B2 | 6/2008 | Lieber et al. |
| 7,399,691 B2 | 7/2008 | Lieber et al. |
| 7,476,596 B2 | 1/2009 | Lieber et al. |

(56) References Cited

U.S. PATENT DOCUMENTS

| | | |
|---|---|---|
| 7,500,213 B2 | 3/2009 | Lieber et al. |
| 7,595,260 B2 | 9/2009 | Lieber et al. |
| 7,619,290 B2 | 11/2009 | Lieber et al. |
| 7,659,165 B2 | 2/2010 | Koenenkamp |
| 7,795,039 B2 | 9/2010 | Spira et al. |
| 7,911,009 B2 | 3/2011 | Lieber et al. |
| 7,915,151 B2 | 3/2011 | Lieber et al. |
| 8,232,584 B2 | 7/2012 | Lieber et al. |
| 8,575,663 B2 * | 11/2013 | Lieber et al. .................. 257/253 |
| 9,102,521 B2 | 8/2015 | Lieber et al. |
| 2001/0054709 A1 | 12/2001 | Heath et al. |
| 2002/0013031 A1 | 1/2002 | Chen et al. |
| 2002/0040805 A1 | 4/2002 | Swager |
| 2002/0055239 A1 | 5/2002 | Tuominen et al. |
| 2002/0084502 A1 | 7/2002 | Jang et al. |
| 2002/0086335 A1 | 7/2002 | Massey et al. |
| 2002/0112814 A1 | 8/2002 | Hafner et al. |
| 2002/0117659 A1 * | 8/2002 | Lieber et al. ................... 257/14 |
| 2002/0122766 A1 | 9/2002 | Lieber et al. |
| 2002/0130311 A1 | 9/2002 | Lieber et al. |
| 2002/0130353 A1 | 9/2002 | Lieber et al. |
| 2002/0146714 A1 | 10/2002 | Lieber et al. |
| 2002/0146745 A1 | 10/2002 | Natan et al. |
| 2002/0158342 A1 | 10/2002 | Tuominen et al. |
| 2002/0172820 A1 | 11/2002 | Majumdar et al. |
| 2002/0175408 A1 | 11/2002 | Majumdar et al. |
| 2002/0179434 A1 | 12/2002 | Dai et al. |
| 2002/0187504 A1 | 12/2002 | Reich et al. |
| 2003/0001091 A1 | 1/2003 | Nakayama et al. |
| 2003/0003300 A1 | 1/2003 | Korgel et al. |
| 2003/0032892 A1 | 2/2003 | Erlach et al. |
| 2003/0048619 A1 | 3/2003 | Kaler et al. |
| 2003/0073071 A1 | 4/2003 | Fritz et al. |
| 2003/0089899 A1 | 5/2003 | Lieber et al. |
| 2003/0098488 A1 | 5/2003 | O'Keeffe et al. |
| 2003/0113713 A1 | 6/2003 | Glezer et al. |
| 2003/0113940 A1 | 6/2003 | Erlanger et al. |
| 2003/0121764 A1 | 7/2003 | Yang et al. |
| 2003/0124509 A1 | 7/2003 | Kenis et al. |
| 2003/0124717 A1 | 7/2003 | Awano et al. |
| 2003/0129087 A1 | 7/2003 | Barbee, Jr. et al. |
| 2003/0134267 A1 | 7/2003 | Kang et al. |
| 2003/0134433 A1 | 7/2003 | Gabriel et al. |
| 2003/0135971 A1 | 7/2003 | Liberman et al. |
| 2003/0156992 A1 | 8/2003 | Anderson et al. |
| 2003/0186522 A1 | 10/2003 | Duan et al. |
| 2003/0186544 A1 | 10/2003 | Matsui et al. |
| 2003/0189202 A1 | 10/2003 | Li et al. |
| 2003/0197456 A1 | 10/2003 | Den et al. |
| 2003/0200521 A1 | 10/2003 | DeHon et al. |
| 2004/0005723 A1 | 1/2004 | Empedocles et al. |
| 2004/0026684 A1 | 2/2004 | Empedocles |
| 2004/0067530 A1 | 4/2004 | Gruner |
| 2004/0075464 A1 | 4/2004 | Samuelson et al. |
| 2004/0095658 A1 | 5/2004 | Buretea et al. |
| 2004/0106203 A1 | 6/2004 | Stasiak et al. |
| 2004/0110163 A1 | 6/2004 | Kotlyar et al. |
| 2004/0112964 A1 | 6/2004 | Empedocles et al. |
| 2004/0113138 A1 | 6/2004 | DeHon et al. |
| 2004/0113139 A1 | 6/2004 | DeHon et al. |
| 2004/0118448 A1 | 6/2004 | Scher et al. |
| 2004/0133118 A1 | 7/2004 | Llinas |
| 2004/0136866 A1 | 7/2004 | Pontis et al. |
| 2004/0146560 A1 | 7/2004 | Whiteford et al. |
| 2004/0157414 A1 | 8/2004 | Gole et al. |
| 2004/0188721 A1 | 9/2004 | Lieber et al. |
| 2004/0191517 A1 | 9/2004 | Drake |
| 2004/0213307 A1 | 10/2004 | Lieber et al. |
| 2004/0235016 A1 | 11/2004 | Hamers et al. |
| 2004/0262636 A1 | 12/2004 | Yang et al. |
| 2005/0037374 A1 | 2/2005 | Melker et al. |
| 2005/0064185 A1 | 3/2005 | Buretea et al. |
| 2005/0064731 A1 | 3/2005 | Park et al. |
| 2005/0066883 A1 | 3/2005 | Dubrow et al. |
| 2005/0072213 A1 | 4/2005 | Besnard et al. |
| 2005/0079533 A1 | 4/2005 | Samuelson et al. |
| 2005/0079659 A1 | 4/2005 | Duan et al. |
| 2005/0084881 A1 | 4/2005 | Kelley et al. |
| 2005/0084887 A1 | 4/2005 | Samuelson et al. |
| 2005/0100960 A1 | 5/2005 | Dai et al. |
| 2005/0101026 A1 | 5/2005 | Sailor et al. |
| 2005/0106713 A1 | 5/2005 | Phan et al. |
| 2005/0109989 A1 | 5/2005 | Whiteford et al. |
| 2005/0110064 A1 | 5/2005 | Duan et al. |
| 2005/0117441 A1 | 6/2005 | Lieber et al. |
| 2005/0133254 A1 | 6/2005 | Tsakalakos |
| 2005/0147990 A1 | 7/2005 | Samuelson et al. |
| 2005/0147991 A1 | 7/2005 | Samuelson et al. |
| 2005/0161662 A1 | 7/2005 | Majumdar et al. |
| 2005/0181587 A1 | 8/2005 | Duan et al. |
| 2005/0201149 A1 | 9/2005 | Duan et al. |
| 2005/0202615 A1 | 9/2005 | Duan et al. |
| 2005/0212079 A1 | 9/2005 | Stumbo et al. |
| 2005/0214967 A1 | 9/2005 | Scher et al. |
| 2005/0219788 A1 | 10/2005 | Chow et al. |
| 2005/0224778 A1 | 10/2005 | Dubin et al. |
| 2005/0230356 A1 | 10/2005 | Empedocles et al. |
| 2005/0244863 A1 | 11/2005 | Mir |
| 2005/0253137 A1 | 11/2005 | Whang et al. |
| 2005/0257821 A1 | 11/2005 | Ramanathan et al. |
| 2005/0266662 A1 | 12/2005 | Yi |
| 2005/0275010 A1 | 12/2005 | Chen et al. |
| 2005/0287717 A1 | 12/2005 | Heald et al. |
| 2006/0008942 A1 | 1/2006 | Romano et al. |
| 2006/0009003 A1 | 1/2006 | Romano et al. |
| 2006/0019472 A1 | 1/2006 | Pan et al. |
| 2006/0054936 A1 | 3/2006 | Lieber et al. |
| 2006/0057360 A1 | 3/2006 | Samuelson et al. |
| 2006/0160246 A1 | 7/2006 | Massey et al. |
| 2006/0175601 A1 | 8/2006 | Lieber et al. |
| 2006/0237749 A1 | 10/2006 | Lieber et al. |
| 2006/0269927 A1 | 11/2006 | Lieber et al. |
| 2007/0026645 A1 | 2/2007 | Lieber et al. |
| 2007/0032023 A1 | 2/2007 | Lieber et al. |
| 2007/0032051 A1 | 2/2007 | Lieber et al. |
| 2007/0032052 A1 | 2/2007 | Lieber et al. |
| 2007/0048492 A1 | 3/2007 | Lieber et al. |
| 2007/0111493 A1 | 5/2007 | Lee et al. |
| 2007/0158766 A1 | 7/2007 | Lieber et al. |
| 2007/0252136 A1 | 11/2007 | Lieber et al. |
| 2007/0281156 A1 | 12/2007 | Lieber et al. |
| 2008/0161876 A1 | 7/2008 | Wirbisky et al. |
| 2008/0191196 A1 | 8/2008 | Lu et al. |
| 2008/0211040 A1 | 9/2008 | Lieber et al. |
| 2008/0254291 A1 | 10/2008 | Lieber et al. |
| 2009/0004852 A1 | 1/2009 | Lieber et al. |
| 2009/0057650 A1 | 3/2009 | Lieber et al. |
| 2009/0299213 A1 | 12/2009 | Patolsky et al. |
| 2010/0022012 A1 | 1/2010 | Lieber et al. |
| 2010/0087013 A1 | 4/2010 | Lieber et al. |
| 2010/0152057 A1 | 6/2010 | Lieber et al. |
| 2010/0227382 A1 | 9/2010 | Lieber et al. |
| 2011/0042641 A1 | 2/2011 | Lieber et al. |
| 2011/0230747 A1 | 9/2011 | Rogers et al. |
| 2011/0315962 A1 | 12/2011 | Lieber et al. |
| 2012/0068156 A1 | 3/2012 | Koley |
| 2012/0267604 A1 | 10/2012 | Tian et al. |
| 2014/0184196 A1 | 7/2014 | Lieber et al. |
| 2015/0137794 A1 | 5/2015 | Lieber et al. |

FOREIGN PATENT DOCUMENTS

| | | |
|---|---|---|
| EP | 1170799 | 1/2002 |
| JP | 07-326603 | 12/1995 |
| JP | 09-191104 | 7/1997 |
| JP | 10-167893 | 6/1998 |
| JP | 2000/31462 | 1/2000 |
| JP | 2001/281965 | 10/2001 |
| WO | WO 91/06036 A1 | 5/1991 |
| WO | WO 96/28538 A1 | 9/1996 |
| WO | WO 96/29629 A2 | 9/1996 |
| WO | WO 97/32571 A1 | 9/1997 |
| WO | WO 97/33737 A1 | 9/1997 |
| WO | WO 97/34025 A1 | 9/1997 |

(56) References Cited

FOREIGN PATENT DOCUMENTS

| WO | WO 97/34140 A1 | 9/1997 |
|---|---|---|
| WO | WO 98/39250 A1 | 9/1998 |
| WO | WO 98/42620 A1 | 10/1998 |
| WO | WO 98/48456 A1 | 10/1998 |
| WO | WO 99/24823 A1 | 5/1999 |
| WO | WO 99/63347 A2 | 12/1999 |
| WO | WO 00/09443 A1 | 2/2000 |
| WO | WO 00/17101 A1 | 3/2000 |
| WO | WO 00/19494 A1 | 4/2000 |
| WO | WO 00/29617 A3 | 5/2000 |
| WO | WO 00/51186 A1 | 8/2000 |
| WO | WO 01/03208 A1 | 1/2001 |
| WO | WO 01/44796 A1 | 6/2001 |
| WO | WO 02/17362 A2 | 2/2002 |
| WO | WO 02/31183 A1 | 4/2002 |
| WO | WO 02/48701 A2 | 6/2002 |
| WO | WO 02/008280 A1 | 10/2002 |
| WO | WO 02/086480 A1 | 10/2002 |
| WO | WO 03/005450 A2 | 1/2003 |
| WO | WO 03/016901 A1 | 2/2003 |
| WO | WO 03/053851 A2 | 7/2003 |
| WO | WO 03/054931 A1 | 7/2003 |
| WO | WO 03/063208 A2 | 7/2003 |
| WO | WO 2004/003535 | 1/2004 |
| WO | WO 2004/010552 A1 | 1/2004 |
| WO | WO 2004/032190 A2 | 4/2004 |
| WO | WO 2004/032193 A2 | 4/2004 |
| WO | WO 2004/034025 A2 | 4/2004 |
| WO | WO 2004/038767 A2 | 5/2004 |
| WO | WO 2004/096699 A1 | 11/2004 |
| WO | WO 2004/109282 A1 | 12/2004 |
| WO | WO 2005/059506 A2 | 6/2005 |
| WO | WO 2005/089165 | 9/2005 |
| WO | WO 2005/093831 A1 | 10/2005 |
| WO | WO 2005/094440 | 10/2005 |
| WO | WO 2005/114282 A2 | 12/2005 |
| WO | WO 2005/119753 A2 | 12/2005 |
| WO | WO 2006/107312 A1 | 10/2006 |
| WO | WO 2006/132659 A2 | 12/2006 |
| WO | WO 2007/044034 A2 | 4/2007 |
| WO | WO 2007/145701 A2 | 12/2007 |
| WO | WO 2008/027078 A2 | 3/2008 |
| WO | WO 2008/033303 A2 | 3/2008 |
| WO | WO 2008/123869 A2 | 10/2008 |
| WO | WO 2008/127314 A1 | 10/2008 |
| WO | WO 2009/104056 A1 | 8/2009 |
| WO | WO 2012/170630 A2 | 12/2012 |
| WO | WO 2013/166259 A1 | 11/2013 |
| WO | WO 2014/031709 A1 | 2/2014 |
| WO | WO 2014/043341 A1 | 3/2014 |

OTHER PUBLICATIONS

European Office Action for Application No. EP 07852353.7 mailed Oct. 1, 2013.
International Search Report and Written Opinion from International Application No. PCT/US2007/006545 mailed Apr. 10, 2008.
International Preliminary Report on Patentability from International Application No. PCT/US2007/006545 mailed Sep. 25, 2008.
European Office Action for Application No. EP 07861323.9 mailed Jun. 26, 2009.
European Office Action for Application No. EP 07861323.9 mailed Jan. 5, 2010.
Invitation to Pay Additional Fees from International Application No. PCT/US2007/013700 mailed Jun. 11, 2008.
International Preliminary Report on Patentability from International Application No. PCT/US2007/013700 mailed Dec. 31, 2008.
International Preliminary Report on Patentability from International Application No. PCT/US2007/024126 mailed Mar. 11, 2009.
Invitation to Pay Additional Fees from International Application No. PCT/US2010/050199 mailed Nov. 26, 2010.
International Search Report and Written Opinion from International Application No. PCT/US2010/050199 mailed Feb. 7, 2011.
International Preliminary Report on Patentability from International Application No. PCT/US2010/050199 issued Mar. 27, 2012.
International Search Report and Written Opinion from International Application No. PCT/US2012/041253 mailed Dec. 26, 2012.
Invitation to Pay Additional Fees from International Application No. PCT/US2013/039228 mailed Jun. 25, 2013.
International Search Report and Written Opinion from International Application No. PCT/US2013/039228 mailed Aug. 30, 2013.
International Search Report and Written Opinion from International Application No. PCT/US2013/055910 mailed Nov. 14, 2013.
Office Action from U.S. Appl. No. 12/225,142 dated Nov. 3, 2011.
Office Action from U.S. Appl. No. 12/225,142 dated Apr. 12, 2012.
Office Action from U.S. Appl. No. 12/225,142 dated Sep. 19, 2012.
Office Action from U.S. Appl. No. 12/225,142 dated May 24, 2013.
Office Action from U.S. Appl. No. 12/225,142 dated Oct. 22, 2013.
Restriction Requirement from U.S. Appl. No. 12/308,207 dated Oct. 19, 2012.
Office Action from U.S. Appl. No. 12/308,207 dated Apr. 5, 2013.
Office Action from U.S. Appl. No. 12/308,207 dated Oct. 21, 2013.
Office Action from U.S. Appl. No. 11/501,466 dated Mar. 30, 2010.
Office Action from U.S. Appl. No. 12/312,740 dated Sep. 6, 2012.
Office Action from U.S. Appl. No. 12/312,740 dated Mar. 7, 2013.
Restriction Requirement from U.S. Appl. No. 13/497,852 dated Jul. 5, 2013.
Office Action from U.S. Appl. No. 13/497,852 dated Sep. 16, 2013.
[No Author Listed] DIG Reagents and Kits for Non-Radioactive Nucleic Acid Labeling and Detection: TeloTAGGG Telomere Length Assay. Roche Applied Science. <http://www.roche-applied-science.com/DIG/dig_prod_telomere_length.thm> Last accessed Apr. 5, 2005. 3 pages.
Blackledge et al., Catalytic Activity of Silanols on Carbamate-Functionalized Surface Assemblies: Monoalkoxy versus Trialkoxy Silanes. Langmuir. Sep. 1999;15(23):8119-25.
Bozovic et al., Electronic properties of mechanically induced kinks in single-walled carbon nanotubes. Applied Physics Letters. Jun. 4, 2001;78(23):3693-5.
Bradley et al., "Integration of Cell Membranes and Nanotube Transistors," Nano Letters (2005) 5, 841-845.
Choe, Modulated Nanowire Structures for Exploring New Nanoprocessor Architechtures and Approaches to Biosensing. Harvard Univertiy thesis. Cambrdige, MA. Apr. 2013. 146 pages.
Cohen-Karni et al., Graphene and nanowire transistors for cellular interfaces and electrical recording. Nano Lett. Mar. 10, 2010;10(3):1098-102.
De Asis et al., High spatial resolution single multiwalled carbon nanotube electrode for stimulation, recording, and whole cell voltage clamping of electrically active cells. Applied Physics Letters. Oct. 13, 2009;95:153701.
Defrancesco, Telomere without end, amen: Looking into longevity with telomere detection kits. The Scientist: Technology Profile. Mar. 30, 1998. <http://www.the-scientist.com/?articles.view/articleNo/18869/title/Telomere-Without-End--Amen--Looking-Into-Longevity-with-Telomere-Detection-Kits/> Last accessed Apr. 5, 2005. 10 pages.
Duan et al., Intracellular recordings of action potentials by an extracellular nanoscale field-effect transistor. Nat Nanotechnol. Dec. 18, 2011;7(3):174-9. Supporting Information included.
Dunlop et al., High-throughput electrophysiology: an emerging paradigm for ion-channel screening and physiology. Nat Rev Drug Discov. Apr. 2008;7(4):358-68.
Fang et al., Electrical detection of single DNA molecules with silicon nanowire devices. Biophys. J., 551A-551A (2007).
Fromherz, "Electrical interfacing of nerve cells and semiconductor chips" Chemphyschem—A European Journal of Chemical Physics & Physical Chemistry, Wiley VCH, Weinheim, DE, vol. 3, No. 3, Mar. 12, 2002 pp. 276-284, XP002300227.
Fromherz, "Semiconductor chips with ion channels, nerve cells and brain" Physica E—Low-Dimensional Systems and Nanostructures, Elsevier Science BV, NL, vol. 16, No. 1, Jan. 2003, pp. 24-34, XP002300226.
Gabay et al., "Engineered self-organization of neural networks using carbon nanotube clusters," Physica A(2005) 350,611-621.

(56) References Cited

OTHER PUBLICATIONS

Gao et al., Electrostatic potential in a bent piezoelectric nanowire. The fundamental theory of nanogenerator and nanopiezotronics. Nano Letters. Jul. 24, 2007;7(8):2499-505.
Gao et al., Outside looking in: nanotube transistor intracellular sensors. Nano Lett. Jun. 13, 2012;12(6):3329-33. Epub May 22, 2012.
Gao et al., Subthreshold regime has the optimal sensitivity for nanowire FET biosensors. Nano Lett. Feb. 10, 2010;10(2):547-52.
He et al., Synthesis and characterization of phospholipid-modified multiwalled carbon nanotubes. Materials Research Bulletin. 2008;43(1):141-8.
Huang et al., Formation, stability, and mobility of one-dimensional lipid bilayers on polysilicon nanowires. Nano Lett. Nov. 2007;7(11):3355-9. Epub Sep. 27, 2007.
Hyun et al., Orientation specific synthesis of kinked silicon nanowires grown by the vapour-liquid-solid mechanism. Nanotechnology. Mar. 25, 2009;20(12):125606. Epub Mar. 4, 2009. 5 pages.
James et al., "Extracellular Recordings From Patterned Neuronal Networks Using Planar Microelectrode Arrays," IEEE Trans. Biomed. Eng. (2004) 51, 1640-1648.
Jiang et al., Rational growth of branched nanowire heterostructures with synthetically encoded properties and function. Proc Natl Acad Sci U S A. Jul. 26, 2011;108(30):12212-6. Epub Jul. 5, 2011. Supporting Information included.
Kiss et al., High throughput ion-channel pharmacology: planar-array-based voltage clamp. Assay Drug Dev Technol. Feb. 2003;1(1 Pt 2):127-35.
Lee et al., Antibody-based bio-nanotube membranes for enantiomeric drug separations. Science. Jun. 21, 2002;296(5576):2198-200.
Lieber, Nanowires: Building blocks for the assembly of integrated nanosystems. Electron Devices Meeting. pp. 21.1.1-21.1.4 (Dec. 13-15, 2004).
Lovat et al., "Carbon Nanotube Substrates Boost Neuronal Electrical Signaling," Nano Letters (2005) 5, 1107-1110.
Martens et al., Measurement of telomere length in haematopoietic cells using in situ hybridization techniques. Biochem Soc Trans. Feb. 2000;28(2):245-50.
Merz et al., "Silicon Chip Interfaced with a Geometrically Defined Net of Snail Neurons," Adv Funct Mater (2005) 15, 739-744.
Nakamura et al., Simple, rapid, quantitative, and sensitive detection of telomere repeats in cell lysate by a hybridization protection assay. Clin Chem. Oct. 1999;45(10):1718-24.
Offenhausser et al., "Field-Effect transistor array for monitoring electrical activity from mammalian neurons in culture," Biosensors & Bioelectronics (1997) 12, 819-826.
Patolsky et al. "Detection, stimulation, and inhibition of neuronal signals with high-density nanowire transistor arrays" Science, vol. 313, Jun. 25, 2006, pp. 1100-1105, XP002474456.
Patolsky et al., Fabrication of silicon nanowire devices for ultrasensitive, label-free, real-time detection of biological and chemical species. Nat Protoc. 2006;1(4):1711-24.
Qing et al., "Nanowire transistor arrays for mapping neural circuits in acute brain slices," PNAS, vol. 107, No. 5, pp. 1882-1887 (Feb. 2, 2010).
Schrlau et al., Cell electrophysiology with carbon nanopipettes. ACS Nano. Mar. 24, 2009;3(3):563-8.
Singhal et al., Multifunctional carbon-nanotube cellular endoscopes. Nat Nanotechnol. Jan. 2011;6(1):57-64. Epub Dec. 12, 2010.
Tian et al., Single-crystalline kinked semiconductor nanowire superstructures. Nat Nanotechnol. Dec. 2009;4(12):824-9. Epub Oct. 18, 2009.
Tian et al., Three-dimensional, flexible nanoscale field-effect transistors as localized bioprobes. Science. Aug. 13, 2010;329(5993):830-4. Supporting Online Material inlcuded.
Timko et al., Electrical recording from hearts with flexible nanowire device arrays. Nano Lett. Feb. 2009;9(2):914-8.
Voelker et al., "Signal Transmission from Individual Mammalian Nerve Cell to Field-Effect Transistor," Small (2005) 1, 206-210.
Willumsen et al., High throughput electrophysiology: new perspectives for ion channel drug discovery. Receptors Channels. 2003;9(1):3-12.
Wu et al., Growth, branching, and kinking of molecular-beam epitaxial <110> GaAs nanowires. Appl Phys Lett, Oct. 20, 2003;83(16):3368-70.
Canadian Office Action dated Oct. 14, 2014 for Application No. 2,655,340.
European Office Action dated Jan. 29, 2015 for Application No. 07873479.5.
International Preliminary Report on Patentability from International Application No. PCT/US2013/039228 mailed Nov. 13, 2014.
International Preliminary Report on Patentability from International Application No. PCT/US2013/055910 mailed Mar. 5, 2015.
Office Action mailed Jul. 15, 2014 for U.S. Appl. No. 12/225,142.
Final Office Action mailed Nov. 25, 2014 for U.S. Appl. No. 12/225,142.
Advisory Action mailed May 22, 2014 for U.S. Appl. No. 13/497,852.
Office Action mailed Jun. 24, 2014 for U.S. Appl. No. 13/497,852.
Final Office Action mailed Dec. 4, 2014 for U.S. Appl. No. 13/497,852.
[No Author Listed] Molecular Wire. Wikipedia®:the Free Encyclopedia. Wikimedia Foundation, Inc. Mar. 11, 2015.
Biercuk et al., Electrical Transport in Single-Wall Carbon Nanotubes. Topics Applied Physics. 2008.111:455-93.
Dekker, Carbon Nanotubes as Molecular Quantum Wires. Physics Today. May 1999. 52(5):22-28. doi: 10.1063/1.882658.
Rotkin, From Quantum Models to Novel Effects to New Applications: Theory of Nanotube Devices. Applied Physics of Carbon Nanotubes NanoScience and Technology 2005, pp. 1-39. DOI: 10.1007/3-540-28075-8_1.
Tans et al., Individual single-wall carbon nanotubes as quantum wires. Nature. Apr. 3, 1997. 386: 474-7. doi:10.1038/386474a0.
European Office Action dated Jun. 4, 2015 for Application No. 07873479.5.
Office Action mailed Jun. 3, 2015 for U.S. Appl. No. 12/225,142.
Appell et al., Nanotechnology: Wired for success. Nature. Oct. 10, 2002. 419: 553:5.doi:10.1038/419553a.
Bulashevich et al., Nanotube Devices: A Microscopic Model. JETP Letters. 2002. 75 (4): 205-9.
Calarco et al. Size-dependent Photoconductivity in MBE-Grown GaN-Nanowires. Nano Letters. 2005. 5(5): 981-4.
Duan et al., Intracellular recordings of action potentials by an extracellular nanoscale field-effect transistor. Nat Nanotechnol. Mar. 2012 ;7(3):174-9. Supplementary Information included.
Dürkop et al., Extraordinary mobility in semiconducting carbon nanotubes. Nano Letters. 2004. 4(1):35-9. DOI: 10.1021/nl034841q.
Korotcenkov et al. Chemical Sensors Simulation and Modeling. vol. 5: Electrochemical Sensors. Momentum Press, LLC, New York, 2013. 26 pages. http://techbus.safaribooksonline.com/9781606505960/chapter8_html. Last accessed Jan. 27, 2016.
Léonard et al., Novel Length Scales in Nanotube Devices. The American Physical Society. Physical Review Letters. Dec. 13, 1999. 83 (24): 5174-7.
Ramanathan et al., Individually addressable conducting polymer nanowires array. Nano Letters. 2004. 4(7): 1237-9.
Sekhar et al., Selective growth of silica nanowires in silicon catalysed by Pt thin film. Nanotechnology. Aug. 29, 2006. 17: 4606-13. doi:10.1088/0957-4484/17/18/013.
Sun et al., Finite-size effects in nickel nanowire arrays. Rapid Communications. Physical Review B. Mar. 1, 2000. 61 (10): R6463.
Suryayanshi et al., Electrochemical fountain pen nanofabrication of vertically grown platinum nanowires. Nanotechnology. Feb. 6, 2007. 18: 105305 (4 pages). doi:10.1088/0957-4484/18/10/105305.
Tanner et al., High-Q GaN nanowire resonators and oscillators. Applied Physics Letters. 2007. 91: 203117.
Agarwal, R., et al., "Lasing in Single Cadmium Sulfide Nanowire Optical Cavities," *Nano Letters*, vol. 5, No. 5, pp. 917-920 (2005).

(56) References Cited

OTHER PUBLICATIONS

Balavoine, F., et al., "Helical Crystallization of Proteins on Carbon Nanotubes: A First Step towards the Development of New Biosensors," *Agnew. Chem.*, vol. 38, pp. 1912-1915 (1999).

Chen et al., "Large on-off ratios and negative differential resistance in a molecular electronic device", *Science*, Nov. 19, 1999, 286:1550-51.

Chen, R.J., et al., "Noncovalent functionalization of carbon nanotubes for highly specific electronic biosensors," *PNAS*, vol. 100, No. 9, pp. 4984-4989 (2003).

Cheung et al., "Diameter Controlled Synthesis of Carbon Nanotubes," *J. Phys. Chem B*, 2002, 106:2429-2433.

Choi, K.J., et al., "Enhancement of Ferroelectricity in Strained BaTiO Thin Films," *Science*, vol. 306, pp. 1005-1009 (2004).

Chung et al., "Silico nanowire devices," *App. Phys. Letters*, 2000, 76(15):2069-2070.

Collier et al., "Electronically configurable molecular-based logic gates," *Science*, 1999, 285:391-394.

Cui et al., "Diameter-controlled synthesis of single-crystal silicon nanowires," *Appl. Phys. Letters*, 2001, 78(15): 2214-2216.

Cui et al., "Doping and Electrical Transport in Silicon Nanowires," *J. Phys. Chem.*, 2000, 104(22):5214-5216.

Cui et al., "Functional nanoscale electronic devices assembled using silicon nanowire building blocks", *Science*, Feb. 2, 2001, 291:851-853.

Cui et al., "High performance silicon nanowire field effect transistors", *NANO Letters*, 3:2 (2003) pp. 149-152.

Cui et al., "Nanowire nanosensors for highly sensitive and selective detection of biological and chemical species", *Science*, Aug. 17, 2001, 293:1289-1292.

Cui, Y. et al. "High Performance Silicon Nanowire Field Effect Transistors" Nano Letters, vol. 3, p. 149, Nov. 1, 2002.

Deng, F., et al., "Salicidation process using NiSi and its device application," *J. Appl. Phys.*, vol. 81, No. 12, pp. 8047-8051 (1997).

Duan et al., "General Synthesis of Compound Semiconductor Nanowires," *Adv. Mat.*, 2000, 12(4):298-302.

Duan et al., "High-performance thin-film transistors using semiconductor nanowires and nanoribbons," *Nature*, 2003, 425:274-278.

Duan et al., "Laser-Assisted Catalytic Growth of Single Crystal GaN Nanowires," *J.Am.Chem.Soc.*, 2000, 122:188-189.

Duan et al., "Nonvolatile Memory and Programmable Logic from Molecule-Gated Nanowires," *Nano Letters*, 2002, 2(5):487-490.

Duan et al.., "Indium phosphide nanowires as building blocks for nanoscale electronic and optoelectronic devices," *Nature*, Jan. 4, 2001, 409:66-69.

Duan, X., et al., "Single-nanowire elecrtrically driven lasers," *Nature*, vol. 421, pp. 241-245(2003).

Duan, X., et al., "Synthesis and optical properties of gallium arsenide nanowires," *Applied Physics Letters*, vol. 76, No. 9, pp. 1116-1118 (2000).

Esfarjani et al., "Electronic and transport properties of N—P doped nanotubes," *Applied Physics Letters*, 1999, 74:79-81.

European Office Action from European Application No. 07873479.5-1240 dated Sep. 25, 2009.

European Office Action from European Application No. 07873479.5 dated Apr. 7, 2010.

Fagan, S., et al., "Ab initio calculation for a hypothetical material: Silicon nanotubes," *Physical Review*, vol. 61, No. 15, pp. 9994-9996 (2000).

Friedman, R.S., et al., "High-speed integrated nanowire circuits," *Nature*, vol. 434, pp. 1085 (2005).

Givargizov, "Fundamental aspects of VSL growth", *Journal of Crystal Growth*, 1975, 31:20-30.

Gradecak, S., et al., "GaN nanowire lasers with low lasing thresholds," *Applied Physics Letters*, vol. 87, pp. 173111 (2005).

Gudiksen et al., "Diameter-Selective Synthesis of Semiconductor Nanowires," *J.Am.Chem.Soc.*, 2000, 122, 8801-8802.

Gudiksen et al., "Growth of nanowire superlattice structures for nanoscale photonics and electronics", *Nature*, 2002, 415:617-620.

Gudiksen et al., "Size-Dependent Photoluminescence from Single Indium Phosphide Nanowires," *J. Phys. Chem.*, 2002, 106:4036-4039.

Gudiksen et al., "Synthetic Control of the Diameter and Length of Single Crystal Semiconductor Nanowires," *J. Phys. Chem.*, 2001, 105:4062-4064.

Guo et al., "Nanoscale silicon field effect transistors fabricated using implant lithography," *Appl. Phys. Lett.*, 71(13):1881-1883.

Hahm, J., et al., "Direct Ultrasensitive Electrical Detection of DNA and DNA Sequence Variations Using Nanowire Nanosensors," *Nano Letters*, vol. 4, No. 1, pp. 51-54 (2004).

Haraguchi et al., "GaAs p-n junction formed in quantum wire crystals," *App. Phys. Letters*, 1992, 60(6):745-747.

Haraguchi et al., "Polarization dependence of light emitted from GaAs p-n junctions in quantum wire crystals", *Journal of Applied Physics*, Apr. 1994, 75(8): 4220-4225.

Heath, J. R., et al., "A liquid solution synthesis of single crystal germanium quantum wires," *Chemical Physics Letters*, vol. 208, No. 3, 4, pp. 263-268 (1993).

Hiruma et al., "Self-organized growth of GaAs/InAs heterostructure nanocylinders by organometallic vapor phase epitaxy", *Journal of Crystal Growth*, 1996, 163: 226-231.

Hiruma, et al., "GaAs fr e-standing quantum-siz wires," *J. Appl. Phys.*, vol. 74, No. 5, pp. 3162 (1993).

Holmes et al., "Control of Thickness and Orientation of Solution-Grown Silicon Nanowires," *Science*, 2000, 287:1471-1473.

Hsu et al., "MFMox Ferroelectric Transistor," Nonvolatile Memory Technology Symposium, Orlando, FL, Nov. 15-17, 2004, p. 24-27.

Hu et al., "Chemistry and Physics in One Dimension: Synthesis and Properties of Nanowires and Nanotubes," *Acc. Chem. Res.*, 1999, 32(5):435-445.

Hu et al., "Controlled growth and electrical properties of heterojunctions of carbon nanotubes and silicon nanowires," *Nature*, 1999, 399:48-51.

Hu et al., "Serpentine Superlattice Nanowire-Array Lasers," *IEEE J. Quantum Elec.*, 1995, 31(8):1380-1388.

Huang et al., "Directed assembly of one-dimensional nanostructures into functional networks", *Science*, Jan. 26, 2001, 291: 630-633.

Huang et al., "Gallium Nitride Nanowire Nanodevices," *Nano Letters*, 2002, 2(2):101-104.

Huang et al., "Logic Gates and Computation from Assembled Nanowire Building Blocks," *Science*, 2001, 294:1313-1317.

Huang et al., "Room-Temperature Ultraviolet Nanowire Nanolasers," *Science*, 2001, 292:897-1898.

Japanese Office Action from Application JP 2003-511316 dated Nov. 9, 2010.

Javey, A., et al., "Ballistic carbon nanotube field-effect transistors," *Nature*, vol. 424, pp. 654 (2003).

Jensen, et al., "Kinetics for Hybridization of Peptide Nucleic Acids (PNA) with DNA and RNA Studied with the BIAcore Technique," *Biochemistry*, vol. 36, pp. 5072-5077 (1997).

Jin et al., "Scalable Interconnection and Integration of Nanowire Devices without Registration," *NanoLetters*, 2004, 4(5):915-919.

Johnson et al., "Single gallium nitride nanowire lasers," *Nature*, 2002, 1: 106-110.

Johnson et al., "Single Nanowire Lasers," *J. Phys. Chem.*, 2001, 105(46):11387-11390.

Joselevich et al., "Vectorial Growth of Metallic and Semiconducting Single-Wall Carbon Nanotubes," *Nano Letters*, 2002, 2(10):1137-1141.

Kanjanachuchai et al., "Coulomb blockade in strained-Si nanowires on leaky virtual substrates", *Semiconductor Science and Technology*, 2001, 16:72-76.

Kong et al., "Chemical vapor deposition of methane for single-walled carbon nanotubes," *Chem. Physics Letters*, 1998, 292:567-574.

Kong et al., "Nanotube molecular wires as chemical sensors", *Science*, Jan. 28, 2000, 287: 622-625.

Kong et al., "Synthesis of individual single-walled carbon nanotubes on patterned silicon wafers," *Nature*, 1998, 395:878-881.

Lahoun et al., "Epitaxial core-shell and core-multishell nanowire heterostructures", *Nature*, 2002, 420: 57-61.

(56) References Cited

OTHER PUBLICATIONS

Lahoun et al., "Semiconductor nanowire heterostructures," *Phil. Trans. R. Soc. Lond. A*, 2004, 362:1247-1260.
Law, M., et al., "Nanoribbon Waveguides for Subwavelength Photonics Integration," *Science*, vol. 305, pp. 1269-1274 (2004).
Leff, D.V., et al., "Thermodynamic Control of Gold Nanocrystal Size: Experiment and Theory," *J. Phys. Chem.*, vol. 99, pp. 7036-7041 (1995).
Lei, B., et al., "Nanowire transistors with ferroelectric gate dielectrics: Enhanced performance and memory effects," *Applied Physics Letters*, vol. 84, No. 22, pp. 4553-4555 (2004).
Li et al., "Molecular detection based on conductance quantization of nanowires" Appl Phys Letter, Mar. 6, 2000, 76(10): 1333-1335.
Li, et al., "Fabrication of stable metallic nanowires with quantized conductance," *Nanotechnology*, vol. 10, pp. 221-223 (1999).
Li, et al., "Sequence-Specific Label-Free DNA Sensors Based on Silicon Nanowires," *Nano Letters*, vol. 4, No. 2, pp. 245-247 (2004).
Lieber, "Nanoscale Science and Technology: Building a Big Future from Small Things," *MRS Bulletin*, 2003, 486-491.
Lieber, C., "Covalent Ceramics III—Science and Technology of Non-Oxides" Materials Research Society Symposium Proceedings vol. 410, Nov. 27-30, 1995, pp. 103-111.
Lieber, C., "Nanowire Superlattices," *Nano Letters*, vol. 2, No. 2, pp. 81-82 (2002).
Lu, W., et al., "One dimensional hole gas in germanium/silicon nanowire heterostructures," *PNAS*, vol. 102, No. 29, pp. 10046-10051 (2005).
MacBeath, et al., "Printing Proteins as Microarrays for High-Throughput Function Determination," *Science*, vol. 289, pp. 1760 (2000).
Martel, et al., "Single- and multi-wall carbon nanotube field-effect transistors," *Apl. Phys. Lett.*, 1998, 73(17):2447-2449.
McAlpine et al., "High-Performance Nanowire Electronics and Photonics and Nanoscale Patterning on Flexible Plastic Substrates," *Proc. of the IEEE*, 2005, 93(7):1357-1363.
McAlpine et al., "Nanoimprint Lithogrphy for Hybrid Plastic Electronics," *Nano Letters*, 2003, 3(4):443-445.
McAlpine, et al., "High-Performance Nanowire Electronics and Photonics on Glass and Plastic Substrates," *Nano-Letters*, 2003, 3(11):1531-1535.
Menon, V.P., et al., "Fabrication and Evaluation of Nanoelectrode Ensembles," *Anal. Chem.*, vol. 67, pp. 1920-1928 (1995).
Mitchell, et al., "Smart Nanotubes for Bioseparations and Biocatalysis," *JACS*, vol. 124, pp. 11864-11865 (2002).
Mizutani, T., et al., "Fabrication and characterization of carbon nanotube FETs," *Proceedings of SPIE*, vol. 5732, pp. 28-36 (2005).
Morales et al., "A Laser Ablation Method for the Synthesis of Crystalline Semiconductor Nanowires," *Science*, 1998, 279: 208-211.
Musin, R.N., et al., "Structural and electronic properties of epitaxial core-shell nanowire heterostructures," *Physical Review*, vol. 71, pp. 155318-1155381-4 (2005).
Neuman, et al., "Microarray profiling of antiviral antibodies for the development of diagnostics, vaccines, and therapeutics," *Clinical Immunology*, vol. 111, pp. 196-201 (2004).
Nosho, Y., et al., "n-type carbon nanotube field-effect transistors fabricated by using Ca contact electrodes," *Applied Physics Letters*, vol. 86, pp. 073105 (2005).
Office Action dated Jun. 22, 2011 in U.S. Appl. No. 11/543,337.
Office Action dated Jun. 30, 2011 in Japanese Application No. 2003-511316.
Office Action dated Jul. 26, 2011 in Canadian Application No. 2,447,728.
Office Action dated Aug. 9, 2011 in European Application No. 02 759 070.2.
Office Action from Canadian Application No. 2,447,728 dated Jul. 19, 2010.
Office Action from Canadian Application No. 200610139984.7 dated Mar. 24, 2010.
Office Action from Japanese Application No. 2005-549958 dated Apr. 5, 2010.
Office Action from Mexican Application No. MX/A/2007010619 dated Jun. 24, 2010.
Office Action from U.S. Appl. No. 10/020,004 dated Aug. 30, 2005.
Office Action from U.S. Appl. No. 10/020,004 dated Jan. 15, 2003.
Office Action from U.S. Appl. No. 10/020,004 dated Jun. 25, 2004.
Office Action from U.S. Appl. No. 10/020,004 dated Mar. 14, 2005.
Office Action from U.S. Appl. No. 10/588,833 dated Jan. 20, 2010.
Office Action from U.S. Appl. No. 10/588,833 dated Jun. 12, 2009.
Office Action from U.S. Appl. No. 10/588,833 dated May 27, 2010.
Office Action from U.S. Appl. No. 11/012,549 dated Dec. 20, 2006.
Office Action from U.S. Appl. No. 11/501,466 dated Feb. 5, 2009.
Office Action from U.S. Appl. No. 11/582,167 dated Apr. 23, 2007.
Office Action from U.S. Appl. No. 12/038,794 dated Mar. 6, 2009.
Office Action from U.S. Appl. No. 11/543,337 dated Mar. 23, 2010.
Office Action from U.S. Appl. No. 11/807,186 dated Apr. 7, 2010.
Office Action from U.S. Appl. No. 12/459,177 dated Sep. 16, 2010.
Office Action from U.S. Appl. No. 12/792,711 dated Oct. 20, 2010.
Office Action in Japanese Patent Application No. 2008-074167 dated Oct. 8, 2011.
Office Action in Japanese Patent Application No. 2008-209206 dated Sep. 15, 2011.
Padeste et al., "Modular amperometric immunosensor devices", 8th International Conference on Solid-State Sensors an Actuators and Eurosensors, 1995, 487-490.
Patolsky, F., et al., "Nanowire-Based Biosensors," *Analytical Chemistry*, pp. 4261 (2006).
Patolsky, F., et al., "Nanowire sensors for medicine and the life sciences," *Nanomedicine*, vol. 1, No. 1, pp. 51-65 (2006).
Patolsky, F., et al., "Electrical detection of single viruses," *PNAS*, vol. 101, No. 39, pp. 14017-14022 (2004).
Patolsky, F., et al., "Nanowire Nanosensors," *Materials Today*, pp. 20-28 (2005).
Pavesi, L., et al., "Optical gain in silicon nanocrystals," *Nature*, vol. 408, pp. 440-444 (2000).
Qi, P., et al., "Toward Large Arrays of Multiplex Functionalized Carbon Notube Sensors for Highly Sensitive and Selective Molecular Detection," *Nano Letters*, vol. 3, No. 3, pp. 347-351 (2003).
Rueckes et al., "Carbon Nanotube-Based Nonvolatile Random Access Memory for Molecular Computing," *Science*, 2000, 289,:94-97.
Shi, Y., et al., "Long Si nanowires with millimeter-scale length by modified thermal evaporation from Si powder," *Appl. Phys.*, vol. 80, pp. 1733-1736 (2005).
Smalley, et al., "Biochip spots single viruses," *Late Tech. Research News*, Oct. 20, 2004.
Soh, H.T., et al., "Integrated nanotube circuits: Controlled growth and ohmic contacting of single-walled carbon nanotubes," *App. Phys. Lett.*, vol. 75, No. 5, pp. 627 (1999).
Solange et al., "Ab initio calculations for a hypothetical material: Silicon nanotubes" Phys Rev B, Apr. 15, 2000, 61(15): 9994-9996.
Star et al., "Preparation and properties of polymer-wrapped single-walled carbon nanotubes", *Angew. Chem. Int.*, 2001, 40(9): 1721-25.
Takayama et al., "Patterning cells and their environments using multiple laminar fluid flows in capillary networks", Proc. Natl. Acad. Sci., 1999, 96:5545-5548.
Tang, Y.H., et al., "Si nanowires synthesized by laser ablation of mixed SiC and $SiO_2$ powders," *Chemical Physics Letters*, vol. 314, pp. 16-20 (1999).
Tans et al., "Room-temperature transistor based on a single carbon nanotube," *Nature*, 1998, 393: 49-52.
Thess et al., "Crystalline Ropes of Metallic Carbon Nanotubes," *Science*, 1996, 273:483-487.
Tiefenauer et al., "Towards Amperometric Immunosensor Devices", *Biosensors and Bioelectronics*, 1997, 12: 213-223.
Tong, L., et al., "Subwavelength-diameter silica wires for low-loss optical wave guiding," *Nature*, vol. 426, No. 18, pp. 816-819 (2003).
Urban, J. J., et al., "Single-Crystalline Barium Titanate Nanowires," *Adv. Mater.*, vol. 15, No. 5, pp. 423-426 (2003).

(56) References Cited

OTHER PUBLICATIONS

Vossmeyer, T., et al., "Combinatorial approaches toward patterning nanocrystals," *J. Applied Physics*, vol. 84, No. 7, pp. 3664-3670 (1998).

Wang et al., "Highly polarized photoluminescence and photodetection from single indium phosphide nanowires", *Science*, 2001, 293:1455-1457.

Wang et al., "$SiO_2$-enhanced synthesis of Si nanowires by laser ablation," *App. Physics Letters*, 1998, 73(26):3902-3904.

Wang, D., et al., "Rational Growth of Branched and Hyperbranched Nanowire Structures," *Nano Letters*, vol. 4, No. 5, pp. 871-874 (2004).

Wang, W. U., et al., "Label-free detection of small-molecule-protein interactions by using nanowire nanosensors," *PNAS*, vol. 102, No. 9, pp. 3208-3212 (2005).

Wei et al., "Synthesis of Single Crystal Bismuth-Telluride and Lead-Telluride Nanowires for New Thermoelectric Materials," *Mat. Res. Soc. Symp. Proc.*, 2000, 581: 219-223.

Whang, D., et al., "Large-Scale Hierarchical Organization of Nanowire Arrays for Integrated Nanysystems," *Nano Letters*, vol. 3, No. 9, pp. 1255-1259 (2003).

Whang, D., et al., "Nanolithography Using Hierarchically Assembled Nanowire Masks," *Nano Letters*, vol. 3, No. 7, pp. 951-954 (2003).

Wolf et al., "Silicon Processing for the VLSI Era," Lattice Press, VI, 2000, 1:12-13.

Wong et al., "Covalently functionalized nanotubes as nanometre-sized probes in chemistry and biology," *Nature*, 1998, 394:52-55.

Wu et al., "Block-by-Block Growth of Single-Crystalline Si/SiGe Superlattice Nanowires," *Nano Letters*, 2002, 2(2): 83-86.

Wu, et al, "Germanium/carbon core-sheath nanostructures," *App. Phys. Lett.*, vol. 77, No. 1, pp. 43-45 (2000).

Wu, Y., et al., "Controlled Growth and Structures of Molecular-Scale Silicon Nanowires," *Nano Letters*, vol. 4, No. 3, pp. 433-436 (2004).

Wu, Y., et al., "Single-crystal metallic nanowires and metal/semiconductor nanowire heterostructures," *Nature*, vol. 430, pp. 61-64, (2004).

Xiang, J., et al., "Ge/Si nanowire heterostructures as high-performance field-effect transistors," *Nature*, vol. 441, No. 25, pp. 489-493 (2006).

Xie, et al., "Cds/CdSe core/sheath nanostructures obtained from CdSnanowires," *Chem. Commun.*, pp. 1969-1971 (Sep. 3, 1999).

Yamada, "Analysis of submicron carbon nanotube field-effect transistors," *Appl. Phys. Letters*, 2000, 76: 628-630.

Yang et al., "Controlled Growth of ZnO Nanowires and Their Optical Properties," *Adv. Funct. Mater*, 2002, 12(5): 323-331.

Yang, et al., "Wires on water," *Nature*, vol. 425, pp. 243-244 (2003).

Yu et al, "Nanoscale silicon wires synthesized using simple physical evaporation," *Appl. Phys. Letters*, 1998, 72:3458-3460.

Yu, et al., "One-Dimensional silicon nanostructures fabricated by thermal evaporation," *Materials Science & Engineering*, vol. 26, pp. 800-804 (2006).

Yu, J. et al. "Silicon Nanowires: Preparation, Device Fabrication, and Transport Properties" *J. Phys. Chem. B* 2000, 104, 11864-11870.

Yun et al., "Ferroelectric Properties of Individual Barium Titanate Nanowires Investigated by Scanned Probe Microscopy," Nano-Lett, 2:447-450, 2002.

Zhang, Y.F. et al., "One-dimensional growth mechanism of crystalline silicon nanowires" Journal of Crystal Growth 197 (1999) 136-140.

Zhang, Y.F., et al., "Bulk-quantity Si nanowires synthesized by SiO sublimation," *Journal of Crystal Growth*, vol. 212, pp. 115-118 (2000).

Zheng, G., et al., "Multiplexed electrical detection of cancer markers with nanowire sensor arrays," *Nature Biotechnology*, vol. 23, No. 10, pp. 1294-1301 (2005).

Zheng, G., et al., "Synthesis and Fabrication of High-Performance n-Type Silicon Nanowire Transistors," *Adv. Mater.*, vol. 16, No. 21, pp. 1890-1893 (2004).

Zhong et al., "Nanowire Crossbar Arrays as Address Decoders for Integrated Nanosystems," *Science*, 2003, 302:1377-1379.

Zhong, et al., "Coherent Single Charge Transport in Molecular-Scale Silicon Nanowires," *Nano Letters*, vol. 5, No. 6, pp. 1143-1146 (2005).

Zhong, Z., et al., "Synthesis of p-Type Gallium Nitride Nanowires for Electric and Photonic Nanodevices," vol. 3, No. 3, pp. 343-346 (2003).

Zhou et al., "Growth morphology and micro-structural aspects of Si nanowires synthesized by laser ablation," *J. of Crystal Growth*, 1999, 197:129-135.

\* cited by examiner

HIGH-SENSITIVITY NANOSCALE WIRE SENSORS

RELATED APPLICATIONS

This application is a continuation of U.S. application Ser. No. 12/312,740, filed May 22, 2009, entitled "High-Sensitivity Nanoscale Wire Sensors" by Lieber, et al., which is a U.S. National Stage Application of PCT/US2007/024126, filed Nov. 19, 2007, entitled "High-Sensitivity Nanoscale Wire Sensors" by Lieber, et al., which claims the benefit of U.S. Provisional Patent Application Ser. No. 60/860,586, filed Nov. 22, 2006, entitled "High-Sensitivity Nanowire Sensors," by Lieber, et al., each incorporated herein by reference.

GOVERNMENT FUNDING

This invention was made with government support under FA9550-06-1-0062 and FA8650-06-C-7622 awarded by the U.S. Air Force. The government has certain rights in the invention.

FIELD OF INVENTION

Various aspects of the present invention generally relate to nanoscale wire devices and methods for use in determining analytes suspected to be present in a sample.

BACKGROUND

Interest in nanotechnology, in particular sub-microelectronic technologies such as semiconductor quantum dots and nanowires, has been motivated by the challenges of chemistry and physics at the nanoscale, and by the prospect of utilizing these structures in electronic and related devices. Nanoscopic articles might be well-suited for transport of charge carriers and excitons (e.g. electrons, electron pairs, etc.) and thus may be useful as building blocks in nanoscale electronics applications. Nanowires are well-suited for efficient transport of charge carriers and excitons, and thus are expected to be important building blocks for nanoscale electronics and optoelectronics.

Nanoscale wires having selectively functionalized surfaces have been described in U.S. patent application Ser. No. 10/020,004, entitled "Nanosensors," filed Dec. 11, 2001, published as Publication No. 2002/0117659 on Aug. 29, 2002, and as corresponding International Patent Application Serial No. PCT/US01/48230, filed Dec. 11, 2001, published as International Patent Application Publication WO 02/48701 on Jun. 20, 2002 (each incorporated herein by reference). Nanoscale wire sensors have also been described in U.S. patent application Ser. No. 11/501,466, entitled "Nanoscale Sensors," filed Aug. 9, 2006, also incorporated herein by reference. As described, functionalization of the nanoscale wire may permit interaction of the functionalized nanoscale wire with various entities, such as molecular entities, and the interaction induces a change in a property of the functionalized nanowire, which provides a mechanism for a nanoscale sensor device for detecting the presence or absence of an analyte suspected to be present in a sample.

SUMMARY OF THE INVENTION

Various aspects of the present invention generally relate to nanoscale wire devices and methods for use in determining analytes suspected to be present in a sample. The subject matter of the present invention involves, in some cases, interrelated products, alternative solutions to a particular problem, and/or a plurality of different uses of one or more systems and/or articles.

In one aspect, the invention is directed to a method. In one set of embodiments, the methods includes an act of exposing a nanoscale wire, having a reaction entity immobilized relative thereto, to a solution suspected of containing an analyte that the reaction entity is able to bind. In some cases, the nanoscale wire has a Debye screening length, when the nanoscale wire is placed in the solution, that is greater than the average cross-sectional dimension of the nanoscale wire. In certain instances, the method also includes an act of operating the nanoscale wire under conditions wherein the nanoscale wire has a conductance that is not linearly proportional to voltage applied to voltage applied to the nanoscale wire.

The method, in another set of embodiments, includes acts of causing an analyte to bind to a nanoscale wire having a reaction entity immobilized relative thereto, and determining a change in charge of the analyte of less than about $10^{-17}$ C.

The invention is directed to an article in another aspect. In one set of embodiments, the article includes a nanoscale wire, having a reaction entity immobilized relative thereto, where the nanoscale wire is exposed to a solution, such that the nanoscale wire has a Debye screening length in the solution that is greater than the average cross-sectional dimension of the nanoscale wire.

In another set of embodiments, the article includes a nanoscale wire, having a reaction entity immobilized relative thereto, where the nanoscale wire can determine a change in charge of an analyte of less than about $10^{-17}$ C.

In another aspect, the present invention is directed to a method of making one or more of the embodiments described herein, for example, a sensing device comprising a nanoscale wire. In yet another aspect, the present invention is directed to a method of using one or more of the embodiments described herein, for example, a sensing device comprising a nanoscale wire.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
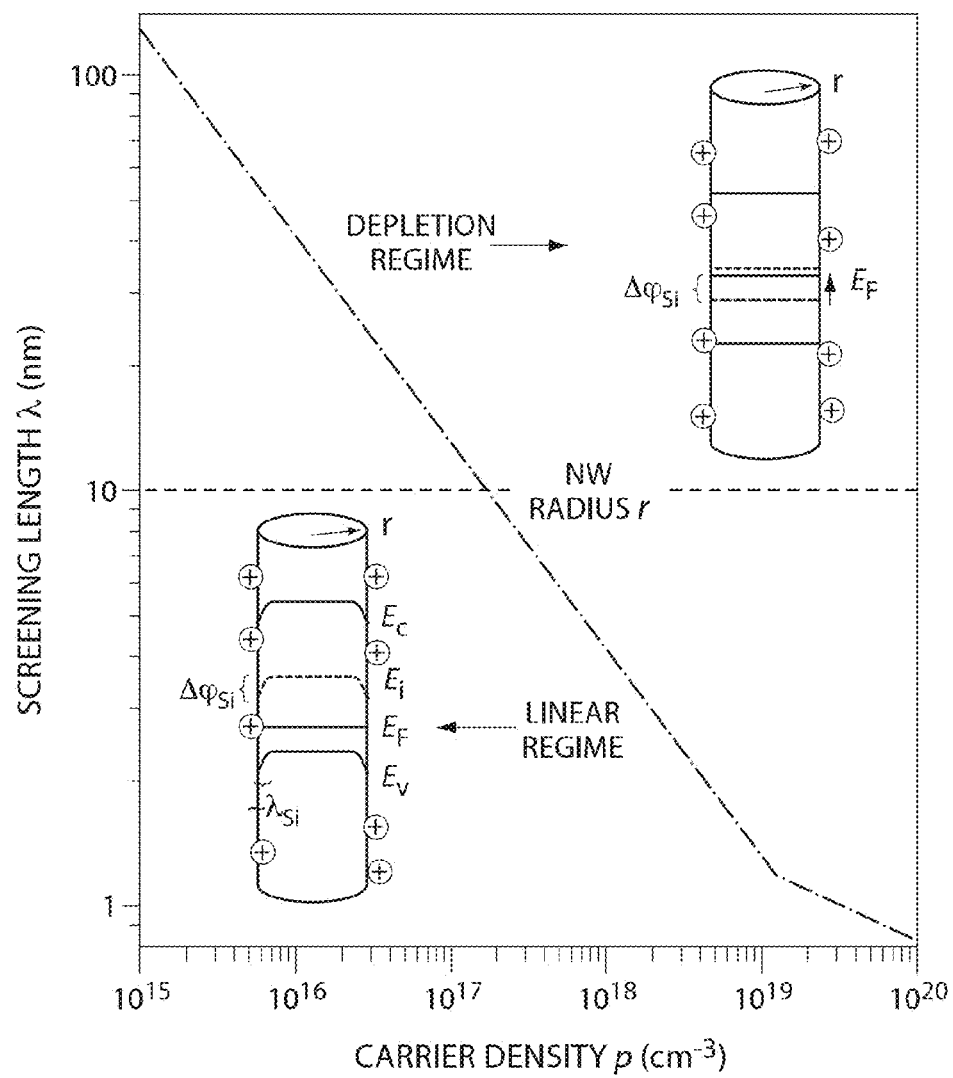
FIG. 1 shows the screening effect of a nanoscale wire used as a sensor, in one embodiment of the invention.

Various aspects of the present invention generally relate to nanoscale wire devices and methods for use in determining analytes suspected to be present in a sample. One aspect of the invention provides a nanoscale wire that has improved sensitivity, for example, as the carrier concentration in the wire is controlled by an external gate voltage, and in some embodiments, the nanoscale wire can be used to determine a change in charge of less than about $10^{-17}$ C. The nanoscale wire, in some cases, may be part of a field effect transistor (FET). In one set of embodiments, the nanoscale wire has a Debye screening length that is greater than the average cross-sectional dimension of the nanoscale wire when the nanoscale wire is exposed to a solution suspected of containing an analyte. In certain instances, the Debye screening length associated with the carriers inside nanoscale wire may be adjusted by adjusting the voltage, for example, a gate voltage applied to an FET structure. In some cases, the nanoscale wire can be operated under conditions where the carriers in the nanoscale wire are depleted and the nanoscale wire has a conductance that is not linearly proportional to the voltage applied to the nanoscale wire sensor device, for example, via a gate electrode. Other aspects of the invention include assays, sensors, kits, and/or other devices that include such nanoscale wires, methods of making and/or using functionalized nanoscale wires (for example, in drug screening or high-throughput screening), and the like.

In general, various aspects of the present invention provide a sensing element comprising a nanoscale wire able to interact with one or more analytes. For example, the nanoscale wire may be used to determine an analyte as part of an assay for determining or diagnosing cancer or other medical conditions (e.g., by determining a suitable marker, for example, a hormone, an enzyme, a peptide, a virus, etc., and diagnosing the cancer or other medical condition based on the determination of the marker), for determining drugs (e.g., as part of a drug assay or a drug screen, for instance, to identify a drug able to treat a medical condition such as cancer or aging), for determining toxins or other environmental agents (e.g., by determining binding of the toxin to a receptor), or the like.

Although the invention is generally described herein in reference to a nanoscale wire, it should be understood that the invention is not limited to nanoscale wires. Many of the methods described herein can be applied to any nanomaterials or nanostructures whose properties are affected by the binding of analyte molecules on the surface. As a non-limiting example, the methods of the present invention may be applied to a FET sensor device comprising nanoparticles that an analyte is able to bind. For instance, a nanoparticle (or other nanostructure) may be exposed to a solution such that the nanoparticle has a Debye screening length, when the nanoparticle is placed in the solution, that is greater than the average cross-sectional dimension of the nanoparticle or other nanostructure, or the sensor may be operated under conditions in which the nanoparticle (or other nanostructure) has a conductance that is not linearly proportional to voltage applied to voltage applied to the nanoparticle or other nanostructure.

The nanoscale wire may have a reaction entity able to interact with an analyte of interest. Nanoscale sensing elements of the invention may be used, for example, to determine pH or metal ions, viruses, proteins or enzymes, nucleic acids (e.g. DNA, RNA, PNA, etc.), drugs, sugars, carbohydrates, a toxin (e.g., a harmful chemical, such as a chemical produced by a living organism that is harmful to other organisms), small molecules (e.g., having molecular weights of less than about 2000 Da, less than about 1500 Da, or less than about 1000 Da), or other analytes of interest, as further described herein. The analyte may be charged, or uncharged in some embodiments. In certain embodiments, single entities may be determined, for example, a single virus, a single protein, a single enzyme, a single nucleic acid molecule, a single drug molecule, a single carbohydrate molecule, etc. In some cases, the sensing element includes a detector constructed and arranged to determine a change in a property of the nanoscale wire, for example, a change in light emission, a change in stress or shape, or a change in an electrical property of the nanoscale wire, such as voltage, current, conductivity, resistivity, inductance, impedance, electrical change, an electromagnetic change, etc. In one set of embodiments, at least a portion of the nanoscale wire is addressable by a sample (e.g., a gas or liquid sample) containing, or at least suspected of containing, the analyte. The term "addressable," e.g., by a fluid, is defined as the ability of the fluid to be positioned relative to the nanoscale wire so that the analytes suspected of being in the fluid are able to interact with the nanoscale wire. The fluid may be proximate to or in contact with the nanoscale wire. In some embodiments, the fluid may be directed to the nanoscale wire through the use of a microfluidic channel, as further described below.

As used herein, the term "reaction entity" refers to any entity that can interact with an analyte in such a manner as to cause a detectable change in a property of a nanoscale wire. The reaction entity may comprise a binding partner to which the analyte binds. The reaction entity, when a binding partner, can comprise a specific binding partner of the analyte. In some cases, the reaction entity can form a coating on the nanoscale wire. Non-limiting examples of reaction entities include a nucleic acid (e.g., DNA or RNA), an antibody, a sugar or a carbohydrate, a protein or an enzyme, a ganglioside or a surfactant, etc., e.g., as discussed herein.

In one set of embodiments, a reaction entity associated with the nanoscale wire is able to interact with an analyte. The reaction entity, as "associated" with or "immobilized" relative to the nanoscale wire, may be positioned in relation to the nanoscale wire (e.g., in close proximity or in contact) such that the analyte can be determined by determining a change in a characteristic or property of the nanoscale wire. Interaction of the analyte with the reaction entity may cause a detectable change or modulation in a property of the nanoscale wire, for example, through electrical coupling with the reaction entity. The term "electrically coupled" or "electrocoupling," when used with reference to a nanoscale wire and an analyte, or other moiety such as a reaction entity, refers to an association between any of the analyte, other moiety, and the nanoscale wire such that electrons can move from one to the other, or in which a change in an electrical characteristic of one can be determined by the other. This can include electron flow between these entities, or a change in a state of charge, oxidation, or the like, that can be determined by the nanoscale wire. As examples, electrical coupling or immobilization can include direct covalent linkage between the analyte or other moiety and the nanoscale wire, indirect covalent coupling (for instance, via a linker, and/or a plurality of linkers, e.g., serially), direct or indirect ionic bonding between the analyte (or other moiety) and the nanoscale wire, direct or indirect bonding of both the analyte and the nanoscale wire to a particle (i.e., the particle acts as a linker between the analyte and the nanoscale wire), direct or indirect bonding of both the analyte and the nanoscale wire to a common surface (i.e., the surface acts as a linker), or other types of bonding or interactions (e.g. hydrophobic interactions or hydrogen bonding). In some cases, no actual covalent bonding is required; for example, the analyte or other moiety may simply be contacted with the nanoscale wire surface. There also need not necessarily be any contact between the nanoscale wire and the analyte or other moiety where the nanoscale wire is sufficiently close to the analyte to permit electron tunneling between the analyte and the nanoscale wire.

Thus, the reaction entity may be positioned relative to the nanoscale wire to cause a detectable change in the nanoscale wire. In some cases, the reaction entity may be positioned within about 100 nm of the nanoscale wire, within about 75 nm of the nanoscale wire, within about 50 nm of the nanoscale wire, within about 20 nm of the nanoscale wire, within about 15 nm of the nanoscale wire, or within about 10 nm of the nanoscale wire. The actual proximity can be determined by those of ordinary skill in the art. In some cases, the reaction entity is positioned less than about 5 nm from the nanoscale wire. In other cases, the reaction entity is positioned within about 4 nm, within about 3 nm, within about 2 nm, or within about 1 nm of the nanoscale wire.

In some embodiments, the reaction entity is fastened to or directly bonded (e.g., covalently) to the nanoscale wire, e.g., as further described herein. However, in other embodiments, the reaction entity is not directly bonded to the nanoscale wire, but is otherwise immobilized relative to the nanoscale wire, i.e., the reaction entity is indirectly immobilized relative to the nanoscale wire. For instance, the reaction entity may be attached to the nanoscale wire through a linker, i.e., a species (or plurality of species) to which the reaction entity and the nanoscale wire are each immobilized relative thereto, e.g., covalently or non-covalently bound to. As an example, a linker may be directly bonded to the nanoscale wire, and the reaction entity may be directly bonded to the linker, or the reaction entity may not be directly bonded to the linker, but immobilized relative to the linker, e.g., through the use of non-covalent bonds such as hydrogen bonding (e.g., as in complementary nucleic acid-nucleic acid interactions), hydrophobic interactions (e.g., between hydrocarbon chains), entropic interactions, or the like. The linker may or may not be directly bonded (e.g., covalently) to the nanoscale wire.

In one set of embodiments, the sensitivity of the reaction entity to the analyte may be enhanced by selecting conditions in which the Debye screening length of the nanoscale wire is controlled such that the Debye screening length is greater than the average cross-sectional dimension of the nanoscale wire when the nanoscale wire is exposed to a solution suspected of containing the analyte. The Debye screening length can be measured by those of ordinary skill in the art (see, e.g., the examples), and varies as a function of various properties of both the nanoscale wire (e.g., the doping level and/or the dielectric constant) and the environment in which the nanoscale wire is located (e.g., the temperature of the solution).

The Debye length of the nanoscale wire, in some embodiments, can be determined as:

$$\lambda = \sqrt{\in k_B T/pe^2}$$

where $\in$ is the electric constant of wire material, p is the carrier concentration in the nanowire, $k_B$ is the Boltzmann constant (sometimes also k), T is the temperature, and e is the elementary charge. The Debye length of nanoscale wire can be adjusted in some cases by controlling the voltage of the nanoscale wire, e.g., in the gate of a FET comprising the nanoscale wire, which may change the carrier concentration inside wire. In some embodiments, the Debye length may be controlled to be longer than the cross-sectional dimension of the nanoscale wire.

In some embodiments, the Debye screening length (more formally, the Debye-Huckel screening length) of the electrolyte solution is given by:

$$\lambda_D = \sqrt{\frac{\varepsilon_0 \varepsilon_r kT}{2N_A e^2 I}},$$

where I is the ionic strength of the electrolyte, $\in_0$ is the permittivity of free space, $\in_r$ is the dielectric constant of the solution, k is the Boltzmann constant, T is the temperature, $N_A$ is Avogadro's Number, and e is the elementary charge. Those of ordinary skill in the art will be able to determine these values. Additionally, those of ordinary skill in the art will be able to select suitable environmental conditions (e.g., temperature and/or ionic strength of a given solution) to make the Debye-Huckel screening length of the solution longer, thereby increasing the sensitivity of the nanoscale wire. For instance, the screening length may be greater than the average cross-sectional dimension of the nanoscale wire. For example, the ionic strength of a solution may be controlled by controlling the concentration of phosphate and/or other ions (e.g., $K^+$, $Cl^-$, etc.) within the solution.

In another set of embodiments, the sensitivity of the reaction entity to the analyte may be enhanced by operating the nanoscale wire under conditions wherein the nanoscale wire has a conductance that is not linearly proportional to voltage applied to voltage applied to the nanoscale wire, i.e., within the "subthreshold regime." Typically, the conductance will depend substantially exponentially on the voltage applied to the nanoscale wire, e.g., the electrolyte gate voltage if the nanoscale wire is part of an FET.

Operating the nanoscale wire sensor under conditions such as those described above may yield increased sensitivity. For example, in some cases, the nanoscale wire can be used to determine a change in charge of an analyte of less than about $10^{-17}$ C, and in some cases, less than about $5 \times 10^{-18}$ C, less than about $3 \times 10^{-18}$ C, less than about $10^{-18}$ C, or less than about $5 \times 10^{-19}$ C.

In another aspect, the present invention generally relates to the attachment of reaction entities, such as biological entities, to the surfaces of nanoscale wires, in some cases by using covalent bonding. The entity is thus immobilized with respect to the surface of the nanoscale wire. In some embodiments, a linker is used to covalently immobilize the entity with respect to the nanoscale wire. In some cases, the entity may be covalently immobilized with respect to the surface of the nanoscale wire at relatively short distances, depending on the size of the linker and/or the precursors thereof. For instance, the entity may be immobilized at a distance of less than about 20 nm, less than about 15 nm, less than about 10 nm, less than about 9 nm, less than about 8 nm, less than about 7 nm, less than about 6 nm, less than about 5 nm, less than about 4 nm, less than about 3 nm, less than about 2 nm, or less than about 1 nm from the surface of the nanoscale wire. In some cases, the proximity of the entity may control or otherwise affect electronic and/or other properties of the nanoscale wire, for example, the conductivity of the nanoscale wire.

Non-limiting examples of chemistries suitable for attaching entities to surfaces of nanoscale wires, optionally via one or more linkers, include the following. In one set of embodiments of the present invention, the surface of the nanoscale wire may be functionalized, for example, the surface may be functionalized with aldehydes, amines, thiols, or the like, which may form nitrogen-containing or sulfur-containing covalent bonds. For instance, in some embodiments, the reaction entity may be covalently bound to the nanoscale wire through the use of a moiety such as an aldehyde moiety, an amine moiety, and/or a thiol moiety. In certain embodiments, a nanoscale wire may be reacted with an aldehyde, amine, or a thiol in solution to functionalize the nanoscale wire with the appropriate moiety, e.g., such that the surface of the nanoscale wire includes terminal aldehyde, amine, and/or thiol groups. Additional examples are disclosed in U.S. patent application Ser. No. 11/501,466, filed Aug. 9, 2006, entitled "Nanoscale Sensors," by Lieber, et al., incorporated herein by reference.

One or more entities, e.g., reaction entities such as proteins, enzymes, nucleic acids, antibodies, receptors, ligands, etc., may then be reacted with the aldehyde, amine, and/or thiol moieties to covalently bind the entity to the nanoscale wire. In some cases, after the entity has been fastened to the nanoscale wire, the surface of the nanoscale wire, including any unreacted moieties, is then passivated, e.g., blocked with one or more compounds that causes the moieties to become unreactive. Non-limiting examples of such passivating agents include ethanolamine. For example, a solution may be added to the nanowires that includes one or more passivating agents.

Also provided, according to another set of embodiments of the present invention, is a sensing element comprising a nanoscale wire and a detector constructed and arranged to determine a property and/or a change in a property of the nanoscale wire. In some cases, alteration of a property of the nanoscale wire may be indicative of an interaction between a reaction entity and an analyte (e.g., association or dissociation of the reaction entity and the analyte). Where a detector is present, any detector capable of determining a property associated with the nanoscale wire can be used. The property can be electronic, electromagnetic, optical, mechanical, or the like. Examples of electrical or magnetic properties that can be determined include, but are not limited to, voltage, current, conductivity, resistance, impedance, inductance, charge, etc. Examples of optical properties associated with the nanoscale wire include its emission intensity and/or emission wavelength, e.g. where the nanoscale wire is emissive. In some cases, the detector will include a power source and a metering device, for example a voltmeter or an ammeter.

In one embodiment, a conductance (or a change in conductance) less than about 1 nS in a nanoscale wire sensor of the invention can be detected. In another embodiment, a conductance in the range of thousandths of a nS can be detected. In other embodiments, conductances of less than about 10 microsiemens, less than about 1 microsiemen, less than about 100 nS, or less than about 10 nS can be detected. The concentration of a species, or analyte, may be detected from femtomolar concentrations, to nanomolar, micromolar, millimolar, and to molar concentrations and above. By using nanoscale wires with known detectors, sensitivity can be extended to a single molecules in some cases.

As a non-limiting example, a charged analyte may be determined by determining a change in an electrical property of the nanoscale wire, for example, conductivity. Immobilizing a charged analyte relative to the nanoscale wire may cause a change in the conductivity of the nanoscale wire, and in some cases, the distance between the charged analyte and the nanoscale wire may determine the magnitude of the change in conductivity of the nanoscale wire. Uncharged analytes can be similarly determined, for instance, by causing the analyte to become charged, e.g., by altering environmental conditions such as pH (by raising or lowering pH), temperature, reactants, or the like, by reacting the analyte with a charged moiety, or the like.

The analyte to be determined by the nanoscale sensor may be present within a sample. The term "sample" refers to any cell, lysate, tissue, or fluid from a biological source (a "biological sample"), or any other medium, biological or non-biological, that can be evaluated in accordance with the invention. The sample may be, for instance, a liquid (e.g., a solution or a suspension) or a gas. A sample includes, but is not limited to, a biological sample drawn from an organism (e.g. a human, a non-human mammal, an invertebrate, a plant, a fungus, an algae, a bacteria, a virus, etc.), a sample drawn from food designed for human consumption, a sample including food designed for animal consumption such as livestock feed, milk, an organ donation sample, a sample of blood destined for a blood supply, a sample from a water supply, a soil sample, or the like.

In some cases, the sample may be a sample suspected of containing an analyte. A "sample suspected of containing" a particular component means a sample with respect to which the content of the component is unknown. For example, a fluid sample from a human suspected of having a disease, but not known to have the disease, defines a sample suspected of containing the disease. "Sample" in this context includes naturally-occurring samples, such as physiological samples from humans or other animals, samples from food, livestock feed, water, soil, etc. Typical samples include tissue biopsies, cells, cell lysates, whole blood, serum or other blood fractions, urine, ocular fluid, saliva, fluid or other samples from tonsils, lymph nodes, needle biopsies, etc.

A variety of sample sizes, for exposure of a sample to a nanoscale sensor of the invention, can be used in various embodiments. As examples, the sample size used in nanoscale sensors may be less than or equal to about 10 microliters, less than or equal to about 1 microliter, or less than or equal to about 0.1 microliter. The sample size may be as small as about 10 nanoliters, 1 nanoliter, or less, in certain instances. The nanoscale sensor also allows for unique accessibility to biological species and may be used for in vivo and/or in vitro applications. When used in vivo, in some case, the nanoscale sensor and corresponding method result in a minimally invasive procedure.

The invention, in some embodiments, involves a sensing element comprising a sample exposure region and a nanoscale wire able to detect the presence or absence of an analyte, and/or the concentration of the analyte. The "sample exposure region" may be any region in close proximity to the nanoscale wire where a sample in the sample exposure region addresses at least a portion of the nanoscale wire. Examples of sample exposure regions include, but are not limited to, a well, a channel, a microfluidic channel, or a gel. In certain embodiments, the sample exposure region is able to hold a sample proximate the nanoscale wire, and/or may direct a sample toward the nanoscale wire for determination of an analyte in the sample. The nanoscale wire may be positioned adjacent or within the sample exposure region. Alternatively, the nanoscale wire may be a probe that is inserted into a fluid or fluid flow path. The nanoscale wire probe may also comprise, in some instances, a microneedle that supports and/or is integral with the nanoscale wire, and the sample exposure region may be addressable by the microneedle. In this arrangement, a device that is constructed and arranged for insertion of a microneedle probe into a sample can include a region surrounding or otherwise in contact with the microneedle that defines the sample exposure region, and a sample in the sample exposure region is addressable by the nanoscale wire, and vice versa. Fluid flow channels can be created at a size and scale advantageous for use in the invention (microchannels) using a variety of techniques such as those described in International Patent Application Serial No. PCT/US97/04005, entitled "Method of Forming Articles and Patterning Surfaces via Capillary Micromolding," filed Mar. 14, 1997, published as Publication No. WO 97/33737 on Sep. 18, 1997, and incorporated herein by reference.

As an example, a sample, such as a fluid suspected of containing an analyte that is to be determined, may be presented to a sample exposure region of a sensing element comprising a nanoscale wire. An analyte present in the fluid that is able to bind to the nanoscale wire and/or a reaction entity immobilized relative to the nanoscale wire may cause a change in a property of the nanoscale wire that is determinable upon binding, e.g. using conventional electronics. If the analyte is not present in the fluid, the relevant property of the nanoscale wire will remain unchanged, and the detector will measure no significant change. Thus, according to this particular example, the presence or absence of an analyte can be determined by monitoring changes, or lack thereof, in the property of the nanoscale wire. In some cases, if the detector measures a change, the magnitude of the change may be a function of the concentration of the analyte, and/or a function of some other relevant property of the analyte (e.g., charge or size, etc.). Thus, by determining the change in the property of the nanoscale wire, the concentration or other property of the analyte in the sample may be determined.

In some embodiments, one or more nanoscale wires may be positioned in a channel or in a microfluidic channel, which may define the sample exposure region in some cases. As used herein, a "channel" is a conduit that is able to transport one or more fluids specifically from one location to another. Materials may flow through the channels, continuously, randomly, intermittently, etc. The channel may be a closed channel, or a channel that is open, for example, open to the external environment. The channel can include characteristics that facilitate control over fluid transport, e.g., structural characteristics, physical/chemical characteristics (e.g., hydrophobicity vs. hydrophilicity) and/or other characteristics that can exert a force (e.g., a containing force) on a fluid when within the channel. The fluid within the channel may partially or completely fill the channel. In some cases the fluid may be held or confined within the channel or a portion of the channel in some fashion, for example, using surface tension (i.e., such that the fluid is held within the channel within a meniscus, such as a concave or convex meniscus). The channel may have any suitable cross-sectional shape that allows for fluid transport, for example, a square channel, a circular channel, a rounded channel, a rectangular channel (e.g., having any aspect ratio), a triangular channel, an irregular channel, etc. The channel may be of any size. For example, the channel may have a largest dimension perpendicular to a direction of fluid flow within the channel of less than about 1000 micrometers in some cases (i.e., a microfluidic channel), less than about 500 micrometers in other cases, less than about 400 micrometers in other cases, less than about 300 micrometers in other cases, less than about 200 micrometers in still other cases, less than about 100 micrometers in still other cases, or less than about 50 or 25 micrometers in still other cases. In some embodiments, the dimensions of the channel may be chosen such that fluid is able to freely flow through the channel. The dimensions of the channel may also be chosen in certain cases, for example, to allow a certain volumetric or linear flowrate of fluid within the channel. Of course, the number of channels, the shape or geometry of the channels, and the placement of channels can be determined by those of ordinary skill in the art.

One or more different nanoscale wires may cross the same microfluidic channel (e.g., at different positions) to detect the same or different analytes, to measure a flowrate of an analyte(s), etc. In another embodiment, one or more nanoscale wires may be positioned in a microfluidic channel to form one of a plurality of analytic elements, for instance, in a microneedle probe, a dip and read probe, etc. The analytic elements probe may be implantable and capable of detecting several analytes simultaneously in real time, according to certain embodiments. In another embodiment, one or more nanoscale wires may be positioned in a microfluidic channel to form an analytic element in a microarray for a cassette or a lab-on-a-chip device. Those of ordinary skill in the art would know of examples of cassette or lab-on-a-chip devices that are suitable for high-throughout chemical analysis and screening, combinational drug discovery, etc. The ability to include multiple nanoscale wires in one nanoscale sensor also allows, in some cases, for the simultaneous detection of different analytes suspected of being present in a single sample, i.e., the nanoscale sensor allows "multiplexed" detection of different analytes. For example, a nanoscale sensor may include a plurality of nanoscale wires that each detect different pH levels, proteins, enzymes, toxins, small molecules, and/or nucleic acids, etc.

In some cases, the sensing element may comprise a plurality of nanoscale wires able to determine (i.e., detect the presence, absence, and/or amount or concentration) one or more analytes within a sample, for example, from a liquid or solution, blood serum, etc., as previously described. Various nanoscale wires within the sensing element may be differentially doped as described herein, and/or contain different reaction entities, and/or the same reaction entities at different concentrations, thereby varying the sensitivity of the nanoscale wires to the analytes, as needed. For example, different reaction entities may be "printed" on the nanoscale wires, e.g., using microarray printing techniques or the like, thereby producing an array of nanoscale wires comprising different reaction entities. In some cases, individual nanoscale wires may be selected based on their ability to interact with specific analytes, thereby allowing the detection of a variety of analytes. The plurality of nanoscale wires may be randomly oriented or parallel to one another, according to another set of embodiments. The plurality of nanoscale wires may also be oriented in an array on a substrate, in specific instances.

A sensing element of the present invention can collect real time data and/or near-real time data, in some embodiments. The data may be used, for example, to monitor the reaction rate of a specific chemical or biological reaction. Physiological conditions or drug concentrations present in vivo may also produce a real time (or near-real time) signal that may be used to control a drug delivery system, in another embodiment of the invention. In addition, electrical determination of one or more properties of the nanoscale wire may allow for the determination of one or more analytes as a function of time. For example, the conductance of a nanoscale wire may be determined as a function of time, which may give additional information regarding the analyte.

In some cases, the nanoscale wires, or at least a portion of the nanoscale wires, may be individually addressable, i.e., the status of the nanoscale wire may be determined without determining the status of nearby nanoscale wires. Thus, for example, a nanoscale wire within a sensing element, or a number of nanoscale wires within the sensing element, may be in electrical communication with an electrode that is able to address the nanoscale wire(s), and such a wire may be addressed using the electrode without addressing other nanoscale wires not in electrical communication with the electrode. For example, a first reaction entity immobilized relative to a first nanoscale wire may bind an analyte, and such a binding event may be detectable independently of the detection of a binding event involving a second reaction entity immobilized relative to a second nanoscale wire. The electrodes may be in electronic communication with one or more electrical contacts.

In some embodiments, the invention includes a microarray including a plurality of sensing regions, at least some of which comprise one or more nanoscale wires. The microarray, including some or all of the sensing regions, may define a sensing element in a sensor device. At least some of the nanoscale wires are able to determine an analyte suspected to be present in a sample that the sensing region of the microarray is exposed to, for example, the nanoscale wire may comprise a reaction entity able to interact with an analyte. If more than one nanoscale wire is present within the sensing region, the nanoscale wires may be able to detect the same analyte and/or different analytes, depending on the application.

In another set of embodiments, an article of the invention may comprise a cassette comprising a sensing element having a sample exposure region and a nanoscale wire. The detection of an analyte in a sample within the sample exposure region may occur, in some cases, while the cassette is disconnected to a detector apparatus, allowing samples to be gathered at one site, and determined at another. The cassette may then be operatively connectable to a detector apparatus able to determine a property associated with the nanoscale wire. As used herein, a device is "operatively connectable" when it has the ability to attach and interact with another apparatus. In other cases, the cassette may be constructed and arranged such that samples may be gathered and determination at one site.

As an example, the present invention includes, in some embodiments, an integrated system comprising a nanoscale wire detector, a reader, and a computer controlled response system. In this example, the nanoscale wire detects a change in the equilibrium or concentration of an analyte in the sample, feeding a signal to the computer controlled response system, causing it to withhold or release a chemical or drug. This is useful as an implantable drug or chemical delivery system because of its small size and low energy requirements. Those of ordinary skill in the art are well aware of the parameters and requirements for constructing implantable devices, readers, and computer-controlled response systems suitable for use in connection with the present invention. That is, the knowledge of those of ordinary skill in the art, coupled with the disclosure herein of nanoscale wires as sensors, enables implantable devices, real-time measurement devices, integrated systems, and the like. Such systems can be made capable of monitoring one, or a plurality of, physiological characteristics individually or simultaneously.

The present invention finds use in a wide range of applications. For instance, in some aspects, any of the techniques described herein may be used in the determination of proteins, enzymes, toxins, viruses, small molecules, or the like, e.g., as in an assay, for example, to detect or diagnose cancer or other medical conditions, toxins or other environmental agents, viruses, or the like. A property of an analyte may be determined by allowing the analyte to interact with a nanoscale wire and/or a reaction entity, and the interaction may be analyzed or determined in some fashion, e.g., quantified. In some cases, the degree or amount of interaction (e.g., a binding constant) may be determined, for example, by measuring a property of the nanoscale wire (e.g., an electronic property, such as the conductance) after exposing the nanoscale wire and/or the reaction entity to the analyte.

In certain instances, such assays are useful in drug screening techniques. In one example, a protein, enzyme, or other target molecule may be immobilized relative to a nanoscale wire as a reaction entity, and exposed to one or more drug candidates, for example, serially or simultaneously. Interaction of the drug candidate(s) with the reaction entity may be determined by determining a property of the nanoscale wire, e.g., as previously described. As a non-limiting example, a nanoscale wire, having an associated reaction entity, may be exposed to one or more species able to interact with the reaction entity, for instance, the nanoscale wire may be exposed to a sample containing a first species able to interact with the reaction entity, where the sample contains or is suspected of containing a second species able to interact with the reaction entity, and optionally other, different species, where one of the species is a drug candidate. As one example, if the reaction entity is an enzyme, the sample may contain a substrate and a drug candidate suspected of interacting with the enzyme in a way that inhibits enzyme/substrate interaction; if the reaction entity is a substrate, the sample may contain an enzyme and a drug candidate suspected of interacting with the substrate in an inhibitory manner; if the reaction entity is a nucleic acid, the sample may contain an enzyme able to bind the nucleic acid (e.g., a nucleic acid synthesis enzyme), or a complementary nucleic acid, and a drug candidate suspected of interacting with the nucleic acid reaction entity in an inhibitory manner; if the reaction entity is a receptor, the sample may contain a ligand for the receptor and a drug candidate suspected of interacting with the receptor in an inhibitory manner; etc. In each of these cases, the drug candidate may also act in a way that enhances, rather than inhibits, interaction.

In some cases, assays of the invention may be used in high-throughput screening applications, e.g., where at least 100, at least 1,000, at least 10,000, or at least 100,000 or more analytes may be rapidly screened, for example, by exposing one or more analytes to a nanoscale wire (e.g., in solution), and/or exposing a plurality of analytes to a plurality of nanoscale wires and/or reaction entities.

Certain aspects of the present invention include a nanoscopic wire or other nanostructured material comprising one or more semiconductor and/or metal compounds, for example, for use in any of the above-described embodiments. In some cases, the semiconductors and/or metals may be chemically and/or physically combined, for example, as in a doped nanoscopic wire. The nanoscopic wire may be, for example, a nanorod, a nanowire, a nanowhisker, or a nanotube. The nanoscopic wire may be used in a device, for example, as a semiconductor component, a pathway, etc. The criteria for selection of nanoscale wires and other conductors or semiconductors for use in the invention are based, in some instances, upon whether the nanoscale wire is able to interact with an analyte, or whether the appropriate reaction entity, e.g. a binding partner, can be easily attached to the surface of the nanoscale wire, or the appropriate reaction entity, e.g. a binding partner, is near the surface of the nanoscale wire. Selection of suitable conductors or semiconductors, including nanoscale wires, will be apparent and readily reproducible by those of ordinary skill in the art with the benefit of the present disclosure.

Many nanoscopic wires as used in accordance with the present invention are individual nanoscopic wires. As used herein, "individual nanoscopic wire" means a nanoscopic wire free of contact with another nanoscopic wire (but not excluding contact of a type that may be desired between individual nanoscopic wires, e.g., as in a crossbar array). For example, an "individual" or a "free-standing" article may, at some point in its life, not be attached to another article, for example, with another nanoscopic wire, or the free-standing article may be in solution. This is in contrast to nanotubes produced primarily by laser vaporization techniques that produce materials formed as ropes having diameters of about 2 nm to about 50 nm or more and containing many individual nanotubes. This is also in contrast to conductive portions of articles which differ from surrounding material only by having been altered chemically or physically, in situ, i.e., where a portion of a uniform article is made different from its surroundings by selective doping, etching, etc. An "individual" or a "free-standing" article is one that can be (but need not be) removed from the location where it is made, as an individual article, and transported to a different location and combined with different components to make a functional device such as those described herein and those that would be contemplated by those of ordinary skill in the art upon reading this disclosure.

In another set of embodiments, the nanoscopic wire (or other nanostructured material) may include additional materials, such as semiconductor materials, dopants, organic compounds, inorganic compounds, etc. The following are non-limiting examples of materials that may be used as dopants within the nanoscopic wire. The dopant may be an elemental semiconductor, for example, silicon, germanium, tin, selenium, tellurium, boron, diamond, or phosphorous. The dopant may also be a solid solution of various elemental semiconductors. Examples include a mixture of boron and carbon, a mixture of boron and P($BP_6$), a mixture of boron and silicon, a mixture of silicon and carbon, a mixture of silicon and germanium, a mixture of silicon and tin, a mixture of germanium and tin, etc. In some embodiments, the dopant may include mixtures of Group IV elements, for example, a mixture of silicon and carbon, or a mixture of silicon and germanium. In other embodiments, the dopant may include mixtures of Group III and Group V elements, for example, BN, BP, BAs, AlN, AlP, AlAs, AlSb, GaN, GaP, GaAs, GaSb, InN, InP, InAs, or InSb. Mixtures of these combinations may also be used, for example, a mixture of BN/BP/BAs, or BN/AlP. In other embodiments, the dopants may include mixtures of Group III and Group V elements. For example, the mixtures may include AlGaN, GaPAs, InPAs, GaInN, AlGaInN, GaInAsP, or the like. In other embodiments, the dopants may also include mixtures of Group II and Group VI elements. For example, the dopant may include mixtures of ZnO, ZnS, ZnSe, ZnTe, CdS, CdSe, CdTe, HgS, HgSe, HgTe, BeS, BeSe, BeTe, MgS, MgSe, or the like. Alloys or mixtures of these dopants are also be possible, for example, ZnCd Se, or ZnSSe or the like. Additionally, mixtures of different groups of semiconductors may also be possible, for example, combinations of Group II-Group VI and Group III-Group V elements, such as $(GaAs)_x(ZnS)_{1-x}$. Other non-limiting examples of dopants may include mixtures of Group IV and Group VI elements, for example GeS, GeSe, GeTe, SnS, SnSe, SnTe, PbO, PbS, PbSe, PbTe, etc. Other dopant mixtures may include mixtures of Group I elements and Group VII elements, such as CuF, CuCl, CuBr, Cut AgF, AgCl, AgBr, AgI, or the like. Other dopant mixtures may include different mixtures of these elements, such as $BeSiN_2$, $CaCN_2$, $ZnGeP_2$, $CdSnAs_2$, $ZnSnSb_2$, $CuGeP_3$, $CuSi_2P_3$, $Si_3N_4$, $Ge_3N_4$, $Al_2O_3$, $(Al, Ga, In)_2(S, Se, Te)_3$, $Al_2CO$, $(Cu, Ag)(Al, Ga, In, Tl, Fe)(S, Se, Te)_2$ or the like.

As a non-limiting example, a p-type dopant may be selected from Group III, and an n-type dopant may be selected from Group V. For instance, a p-type dopant may include at least one of B, Al and In, and an n-type dopant may include at least one of P, As and Sb. For Group III-Group V mixtures, a p-type dopant may be selected from Group II, including one or more of Mg, Zn, Cd and Hg, or Group IV, including one or more of C and Si. An n-type dopant may be selected from at least one of Si, Ge, Sn, S, Se and Te. It will be understood that the invention is not limited to these dopants, but may include other elements, alloys, or mixtures as well.

As used herein, the term "Group," with reference to the Periodic Table, is given its usual definition as understood by one of ordinary skill in the art. For instance, the Group II elements include Mg and Ca, as well as the Group II transition elements, such as Zn, Cd, and Hg. Similarly, the Group III elements include B, Al, Ga, In and Tl; the Group IV elements include C, Si, Ge, Sn, and Pb; the Group V elements include N, P, As, Sb and Bi; and the Group VI elements include O, S, Se, Te and Po. Combinations involving more than one element from each Group are also possible. For example, a Group II-VI material may include at least one element from Group II and at least one element from Group VI, e.g., ZnS, ZnSe, ZnSSe, ZnCdS, CdS, or CdSe. Similarly, a Group III-V material may include at least one element from Group III and at least one element from Group V, for example GaAs, GaP, GaAsP, InAs, InP, AlGaAs, or InAsP. Other dopants may also be included with these materials and combinations thereof, for example, transition metals such as Fe, Co, Te, Au, and the like. The nanoscale wire of the present invention may further include, in some cases, any organic or inorganic molecules. In some cases, the organic or inorganic molecules are polarizable and/or have multiple charge states.

In some embodiments, at least a portion of a nanoscopic wire may be a bulk-doped semiconductor. As used herein, a "bulk-doped" article (e.g. an article, or a section or region of an article) is an article for which a dopant is incorporated substantially throughout the crystalline lattice of the article, as opposed to an article in which a dopant is only incorporated in particular regions of the crystal lattice at the atomic scale, for example, only on the surface or exterior. For example, some articles such as carbon nanotubes are typically doped after the base material is grown, and thus the dopant only extends a finite distance from the surface or exterior into the interior of the crystalline lattice. It should be understood that "bulk-doped" does not define or reflect a concentration or amount of doping in a semiconductor, nor does it necessarily indicate that the doping is uniform. In particular, in some embodiments, a bulk-doped semiconductor may comprise two or more bulk-doped regions. Thus, as used herein to describe nanoscopic wires, "doped" refers to bulk-doped nanoscopic wires, and, accordingly, a "doped nanoscopic (or nanoscale) wire" is a bulk-doped nanoscopic wire. "Heavily doped" and "lightly doped" are terms the meanings of which are understood by those of ordinary skill in the art.

In one set of embodiments, the invention includes a nanoscale wire (or other nanostructured material) that is a single crystal. As used herein, a "single crystal" item (e.g., a semiconductor) is an item that has covalent bonding, ionic bonding, or a combination thereof throughout the item. Such a single-crystal item may include defects in the crystal, but is to be distinguished from an item that includes one or more crystals, not ionically or covalently bonded, but merely in close proximity to one another.

In yet another set of embodiments, the nanoscale wire (or other nanostructured material) may comprise two or more regions having different compositions. Each region of the nanoscale wire may have any shape or dimension, and these can be the same or different between regions. For example, a region may have a smallest dimension of less than 1 micron, less than 100 nm, less than 10 nm, or less than 1 nm. In some cases, one or more regions may be a single monolayer of atoms (i.e., "delta-doping"). In certain cases, the region may be less than a single monolayer thick (for example, if some of the atoms within the monolayer are absent).

The two or more regions may be longitudinally arranged relative to each other, and/or radially arranged (e.g., as in a core/shell arrangement) within the nanoscale wire. As one example, the nanoscale wire may have multiple regions of semiconductor materials arranged longitudinally. In another example, a nanoscale wire may have two regions having different compositions arranged longitudinally, surrounded by a third region or several regions, each having a composition different from that of the other regions. As a specific example, the regions may be arranged in a layered structure within the nanoscale wire, and one or more of the regions may be delta-doped or at least partially delta-doped. As another example, the nanoscale wire may have a series of regions positioned both longitudinally and radially relative to each other. The arrangement can include a core that differs in composition along its length (changes in composition or concentration longitudinally), while the lateral (radial) dimensions of the core do, or do not, change over the portion of the length differing in composition. The shell portions can be adjacent each other (contacting each other, or defining a change in composition or concentration of a unitary shell structure longitudinally), or can be separated from each other by, for example, air, an insulator, a fluid, or an auxiliary, non-nanoscale wire component. The shell portions can be positioned directly on the core, or can be separated from the core by one or more intermediate shells portions that can themselves be constant in composition longitudinally, or varying in composition longitudinally, i.e., the invention allows the provision of any combination of a nanowire core and any number of radially-positioned shells (e.g., concentric shells), where the core and/or any shells can vary in composition and/or concentration longitudinally, any shell sections can be spaced from any other shell sections longitudinally, and different numbers of shells can be provided at different locations longitudinally along the structure.

In still another set of embodiments, a nanoscale wire may be positioned proximate the surface of a substrate, i.e., the nanoscale wire may be positioned within about 50 nm, about 25 nm, about 10 nm, or about 5 nm of the substrate. In some cases, the proximate nanoscale wire may contact at least a portion of the substrate. In one embodiment, the substrate comprises a semiconductor and/or a metal. Non-limiting examples include Si, Ge, GaAs, etc. Other suitable semiconductors and/or metals are described above with reference to nanoscale wires. In certain embodiments, the substrate may comprise a nonmetal/nonsemiconductor material, for example, a glass, a plastic or a polymer, a gel, a thin film, etc. Non-limiting examples of suitable polymers that may form or be included in the substrate include polyethylene, polypropylene, poly(ethylene terephthalate), polydimethylsiloxane, or the like.

In certain aspects, the present invention provides a method of preparing a nanostructure. In one set of embodiments, the method involves allowing a first material to diffuse into at least part of a second material, optionally creating a new compound. For example, the first and second materials may each be metals or semiconductors, one material may be a metal and the other material may be a semiconductor, etc. In one set of embodiments, a semiconductor may be annealed to a metal. For example, a portion of the semiconductor and/or a portion of the metal may be heated such that at least some metal atoms are able to diffuse into the semiconductor, or vice versa. In one embodiment, a metal electrode (e.g., a nickel, gold, copper, silver, chromium electrode, etc.), may be positioned in physical contact with a semiconductor nanoscopic wire, and then annealed such that at least a portion of the semiconductor diffuses into at least a portion of the metal, optionally forming a metal-semiconductor compound, e.g., as disclosed in International Patent Application No. PCT/US2005/004459, filed Feb. 14, 2005, entitled "Nanostructures Containing Metal-Semiconductor Compounds," by Lieber, et al., incorporated herein by reference. For example, the semiconductor may be annealed with the metal at a temperature of about 300° C., about 350° C., about 400° C., about 450° C., about 500° C., about 550° C., or about 600° C. for a period of time of at least about 30 minutes, at least about 1 hour, at least about 2 hours, at least about 4 hours, at least about 6 hours etc. Such annealing may allow, for example, lower contact resistances or impedances between the metal and the semiconductor.

In some cases, the metal may be passivated, e.g., as described herein. For example, the metal, or at least a portion of the metal, may be exposed to one or more passivating agents, for example, $Si_3N_4$. Insulation of the metal by the passivating agent may be used to form a layer covering the surface of the metal, for example, to prevent reaction or nonspecific binding between an analyte and the metal. For instance, a metal electrode may be in electrical communication with a semiconductor comprising one or more immobilized reaction entities, and the metal electrode may be passivated to prevent a reaction or nonspecific binding between the metal and the reaction entity, and/or to reduce or prevent leakage current from the metal. In some cases, the passivation may be conducted at a relatively high temperature, for example, within a plasma CVD chamber.

In certain embodiments, the present invention involves controlling and altering the doping of semiconductors in a nanoscale wire. In some cases, the nanoscale wires (or other nanostructure) may be produced using techniques that allow for direct and controlled growth of the nanoscale wires. In some cases, the nanoscale wire may be doped during growth of the nanoscale wire. Doping the nanoscale wire during growth may result in the property that the doped nanoscale wire is bulk-doped. Furthermore, such doped nanoscale wires may be controllably doped, such that a concentration of a dopant within the doped nanoscale wire can be controlled and therefore reproduced consistently.

Certain arrangements may utilize metal-catalyzed CVD techniques ("chemical vapor deposition") to synthesize individual nanoscale wires. CVD synthetic procedures useful for preparing individual wires directly on surfaces and in bulk form are generally known, and can readily be carried out by those of ordinary skill in the art. Nanoscopic wires may also be grown through laser catalytic growth. With the same basic principles as LCG, if uniform diameter nanoclusters (less than 10% to 20% variation depending on how uniform the nanoclusters are) are used as the catalytic cluster, nanoscale wires with uniform size (diameter) distribution can be produced, where the diameter of the wires is determined by the size of the catalytic clusters. By controlling growth time, nanoscale wires with different lengths can be grown.

One technique that may be used to grow nanoscale wires is catalytic chemical vapor deposition ("C-CVD"). In C-CVD, reactant molecules are formed from the vapor phase. Nanoscale wires may be doped by introducing the doping element into the vapor phase reactant (e.g. diborane and phosphane). The doping concentration may be controlled by controlling the relative amount of the doping compound introduced in the composite target. The final doping concentration or ratios are not necessarily the same as the vapor-phase concentration or ratios. By controlling growth conditions, such as temperature, pressure or the like, nanoscale wires having the same doping concentration may be produced.

Another technique for direct fabrication of nanoscale wire junctions during synthesis is referred to as laser catalytic growth ("LCG"). In LCG, dopants are controllably introduced during vapor phase growth of nanoscale wires. Laser vaporization of a composite target composed of a desired material (e.g. silicon or indium phosphide) and a catalytic material (e.g. a nanoparticle catalyst) may create a hot, dense vapor. The vapor may condense into liquid nanoclusters through collision with a buffer gas. Growth may begin when the liquid nanoclusters become supersaturated with the desired phase and can continue as long as reactant is available. Growth may terminate when the nanoscale wire passes out of the hot reaction zone and/or when the temperature is decreased. The nanoscale wire may be further subjected to different semiconductor reagents during growth.

Other techniques to produce nanoscale semiconductors such as nanoscale wires are also contemplated. For example, nanoscale wires of any of a variety of materials may be grown directly from vapor phase through a vapor-solid process. Also, nanoscale wires may also be produced by deposition on the edge of surface steps, or other types of patterned surfaces. Further, nanoscale wires may be grown by vapor deposition in or on any generally elongated template. The porous membrane may be porous silicon, anodic alumina, a diblock copolymer, or any other similar structure. The natural fiber may be DNA molecules, protein molecules carbon nanotubes, any other elongated structures. For all the above described techniques, the source materials may be a solution or a vapor. In some cases, while in solution phase, the template may also include be column micelles formed by surfactant.

In some cases, the nanoscale wire may be doped after formation. In one technique, a nanoscale wire having a substantially homogeneous composition is first synthesized, then is doped post-synthetically with various dopants. Such doping may occur throughout the entire nanoscale wire, or in one or more portions of the nanoscale wire, for example, in a wire having multiple regions differing in composition.

One aspect of the invention provides for the assembly, or controlled placement, of nanoscale wires on a surface. Any substrate may be used for nanoscale wire placement, for example, a substrate comprising a semiconductor, a substrate comprising a metal, a substrate comprising a glass, a substrate comprising a polymer, a substrate comprising a gel, a substrate that is a thin film, a substantially transparent substrate, a non-planar substrate, a flexible substrate, a curved substrate, etc. In some cases, assembly can be carried out by aligning nanoscale wires using an electrical field. In other cases, assembly can be performed using an arrangement involving positioning a fluid flow directing apparatus to direct fluid containing suspended nanoscale wires toward and in the direction of alignment with locations at which nanoscale wires are desirably positioned.

In certain cases, a nanoscale wire (or other nanostructure) is formed on the surface of a substrate, and/or is defined by a feature on a substrate. In one example, a nanostructure, such as a nanoscale wire, is formed as follows. A substrate is imprinted using a stamp or other applicator to define a pattern, such as a nanoscale wire or other nanoscale structure. After removal of the stamp or other applicator, at least a portion of the imprintable layer is removed, for example, through etching processes such as reactive ion etching (RIE), or other known techniques. In some cases, enough imprintable material may be removed from the substrate so as to expose portions of the substrate free of the imprintable material. A metal or other materials may then be deposited onto at least a portion of the substrate, for example, gold, copper, silver, chromium, etc. In some cases, a "lift-off" step may then be performed, where at least a portion of the imprintable material is removed from the substrate. Metal or other material deposited onto the imprintable material may be removed along with the removal of the imprintable material, for example, to form one or more nanoscale wires. Structures deposited on the surface may be connected to one or more electrodes in some cases. The substrate may be any suitable substrate that can support an imprintable layer, for example, comprising a semiconductor, a metal, a glass, a polymer, a gel, etc. In some cases, the substrate may be a thin film, substantially transparent, non-planar, flexible, and/ or curved, etc.

In certain cases, an array of nanoscale wires may be produced by providing a surface having a plurality of substantially aligned nanoscale wires, and removing, from the surface, a portion of one or more of the plurality of nanoscale wires. The remaining nanoscale wires on the surface may then be connected to one or more electrodes. In certain cases, the nanoscopic wires are arranged such that they are in contact with each other; in other instances, however, the aligned nanoscopic wires may be at a pitch such that they are substantially not in physical contact.

In certain cases, nanoscale wires are positioned proximate a surface using flow techniques, i.e., techniques where one or more nanoscale wires may be carried by a fluid to a substrate. Nanoscale wires (or any other elongated structures) can be aligned by inducing a flow of a nanoscale wire solution on surface, where the flow can include channel flow or flow by any other suitable technique. Nanoscale wire arrays with controlled position and periodicity can be produced by patterning a surface of a substrate and/or conditioning the surface of the nanoscale wires with different functionalities, where the position and periodicity control may be achieved by designing specific complementary forces between the patterned surface and the nanoscale wires. Nanoscale wires can also be assembled using a Langmuir-Blodgett (LB) trough. Nanoscale wires may first be surface-conditioned and dispersed to the surface of a liquid phase to form a Langmuir-Blodgett film. In some cases, the liquid may include a surfactant, which can, in some cases, reduce aggregation of the nanoscale wires and/or reduce the ability of the nanoscale wires to interact with each other. The nanoscale wires can be aligned into different patterns (such as parallel arrays or fibers) by compressing the surface or reducing the surface area of the surface.

Another arrangement involves forming surfaces on a substrate including regions that selectively attract nanoscale wires surrounded by regions that do not selectively attract them. Surfaces can be patterned using known techniques such as electron-beam patterning, "soft-lithography" such as that described in International Patent Application Serial No. PCT/US96/03073, entitled "Microcontact Printing on Surfaces and Derivative Articles," filed Mar. 1, 1996, published as Publication No. WO 96/29629 on Jul. 26, 1996; or U.S. Pat. No. 5,512,131, entitled "Formation of Microstamped Patterns on Surfaces and Derivative Articles," issued Apr. 30, 1996, each of which is incorporated herein by reference. Additional techniques are described in U.S. Patent Application Ser. No. 60/142,216, entitled "Molecular Wire-Based Devices and Methods of Their Manufacture," filed Jul. 2, 1999, incorporated herein by reference. Fluid flow channels can be created at a size scale advantageous for placement of nanoscale wires on surfaces using a variety of techniques such as those described in International Patent Application Serial No. PCT/US97/04005, entitled "Method of Forming Articles and Patterning Surfaces via Capillary Micromolding," filed Mar. 14, 1997, published as Publication No. WO 97/33737 on Sep. 18, 1997, and incorporated herein by reference. Other techniques include those described in U.S. Pat. No. 6,645,432, entitled "Microfluidic Systems Including Three-dimensionally Arrayed Channel Networks," issued Nov. 11, 2003, incorporated herein by reference.

Chemically patterned surfaces other than SAM-derivatized surfaces can be used, and many techniques for chemically patterning surfaces are known. Another example of a chemically patterned surface may be a micro-phase separated block copolymer structure. These structures may provide a stack of dense lamellar phases, where a cut through these phases reveals a series of "lanes" wherein each lane represents a single layer. The assembly of nanoscale wires onto substrate and electrodes can also be assisted using bimolecular recognition in some cases. For example, one biological binding partner may be immobilized onto the nanoscale wire surface and the other one onto a substrate or an electrode using physical adsorption or covalently linking. An example technique which may be used to direct the assembly of a nanoscopic wires on a substrate is by using "SAMs," or self-assembled monolayers. Any of a variety of substrates and SAM-forming material can be used along with microcontact printing techniques, such as those described in International Patent Application Serial No. PCT/US96/03073, entitled "Microcontact Printing on Surfaces and Derivative Articles," filed Mar. 1, 1996, published as Publication No. WO 96/29629 on Jul. 26, 1996, incorporated herein by reference in its entirety.

In some cases, the nanoscale wire arrays may also be transferred to another substrate, e.g., by using stamping techniques. In certain instances, nanoscale wires may be assembled using complementary interaction, i.e., where one or more complementary chemical, biological, electrostatic, magnetic or optical interactions are used to position one or more nanoscale wires on a substrate. In certain cases, physical patterns may be used to position nanoscale wires proximate a surface. For example, nanoscale wires may be positioned on a substrate using physical patterns, for instance, aligning the nanoscale wires using corner of the surface steps or along trenches on the substrate.

In one aspect, the present invention provides any of the above-mentioned devices packaged in kits, optionally including instructions for use of the devices. As used herein, "instructions" can define a component of instructional utility (e.g., directions, guides, warnings, labels, notes, FAQs ("frequently asked questions"), etc., and typically involve written instructions on or associated with packaging of the invention. Instructions can also include instructional communications in any form (e.g., oral, electronic, digital, optical, visual, etc.), provided in any manner such that a user will clearly recognize that the instructions are to be associated with the device, e.g., as discussed herein. Additionally, the kit may include other components depending on the specific application, for example, containers, adapters, syringes, needles, replacement parts, etc. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, replacing, or the like that can be associated with the methods and compositions of the invention, e.g., as discussed herein. Promoting may also include, in some cases, seeking approval from a government agency to sell a composition of the invention for medicinal purposes. Methods of promotion can be performed by any party including, but not limited to, businesses (public or private), contractual or sub-contractual agencies, educational institutions such as colleges and universities, research institutions, hospitals or other clinical institutions, governmental agencies, etc. Promotional activities may include instructions or communications of any form (e.g., written, oral, and/or electronic communications, such as, but not limited to, e-mail, telephonic, facsimile, Internet, Web-based, etc.) that are clearly associated with the invention.

DEFINITIONS

The following definitions will aid in the understanding of the invention. Certain devices of the invention may include wires or other components of scale commensurate with nanometer-scale wires, which includes nanotubes and nanowires. In some embodiments, however, the invention comprises articles that may be greater than nanometer size (e.g., micrometer-sized). As used herein, "nanoscopic-scale," "nanoscopic," "nanometer-scale," "nanoscale," the "nano-" prefix (for example, as in "nanostructured"), and the like generally refers to elements or articles having widths or diameters of less than about 1 micron, and less than about 100 nm in some cases. In all embodiments, specified widths can be a smallest width (i.e. a width as specified where, at that location, the article can have a larger width in a different dimension), or a largest width (i.e. where, at that location, the article has a width that is no wider than as specified, but can have a length that is greater).

As used herein, a "wire" generally refers to any material having a conductivity of or of similar magnitude to any semiconductor or any metal, and in some embodiments may be used to connect two electronic components such that they are in electronic communication with each other. For example, the terms "electrically conductive" or a "conductor" or an "electrical conductor" when used with reference to a "conducting" wire or a nanoscale wire, refers to the ability of that wire to pass charge. Typically, an electrically conductive nanoscale wire will have a resistivity comparable to that of metal or semiconductor materials, and in some cases, the electrically conductive nanoscale wire may have lower resistivities, for example, resistivities of less than about 100 microOhm cm (μΩcm). In some cases, the electrically conductive nanoscale wire will have a resistivity lower than about $10^{-3}$ ohm meters, lower than about $10^{-4}$ ohm meters, or lower than about $10^{-6}$ ohm meters or $10^{-7}$ ohm meters.

A "semiconductor," as used herein, is given its ordinary meaning in the art, i.e., an element having semiconductive or semi-metallic properties (i.e., between metallic and non-metallic properties). An example of a semiconductor is silicon. Other non-limiting examples include gallium, germanium, diamond (carbon), tin, selenium, tellurium, boron, or phosphorous.

A "nanoscopic wire" (also known herein as a "nanoscopic-scale wire" or "nanoscale wire") generally is a wire, that at any point along its length, has at least one cross-sectional dimension and, in some embodiments, two orthogonal cross-sectional dimensions less than 1 micron, less than about 500 nm, less than about 200 nm, less than about 150 nm, less than about 100 nm, less than about 70, less than about 50 nm, less than about 20 nm, less than about 10 nm, or less than about 5 nm. In other embodiments, the cross-sectional dimension can be less than 2 nm or 1 nm. In one set of embodiments, the nanoscale wire has at least one cross-sectional dimension ranging from 0.5 nm to 100 nm or 200 nm. In some cases, the nanoscale wire is electrically conductive. Where nanoscale wires are described having, for example, a core and an outer region, the above dimensions generally relate to those of the core. The cross-section of a nanoscopic wire may be of any arbitrary shape, including, but not limited to, circular, square, rectangular, annular, polygonal, or elliptical, and may be a regular or an irregular shape. The nanoscale wire may be solid or hollow. A non-limiting list of examples of materials from which nanoscale wires of the invention can be made appears below. Any nanoscale wire can be used in any of the embodiments described herein, including carbon nanotubes, molecular wires (i.e., wires formed of a single molecule), nanorods, nanowires, nanowhiskers, organic or inorganic conductive or semiconducting polymers, and the like, unless otherwise specified. Other conductive or semiconducting elements that may not be molecular wires, but are of various small nanoscopic-scale dimensions, can also be used in some instances, e.g. inorganic structures such as main group and metal atom-based wire-like silicon, transition metal-containing wires, gallium arsenide, gallium nitride, indium phosphide, germanium, cadmium selenide, etc. A wide variety of these and other nanoscale wires can be grown on and/or applied to surfaces in patterns useful for electronic devices in a manner similar to techniques described herein involving the specific nanoscale wires used as examples, without undue experimentation. The nanoscale wires, in some cases, may be formed having dimensions of at least about 1 micron, at least about 3 microns, at least about 5 microns, or at least about 10 microns or about 20 microns in length, and can be less than about 100 nm, less than about 80 nm, less than about 60 nm, less than about 40 nm, less than about 20 nm, less than about 10 nm, or less than about 5 nm in thickness (height and width). The nanoscale wires may have an aspect ratio (length to thickness) of greater than about 2:1, greater than about 3:1, greater than about 4:1, greater than about 5:1, greater than about 10:1, greater than about 25:1, greater than about 50:1, greater than about 75:1, greater than about 100:1, greater than about 150:1, greater than about 250:1, greater than about 500:1, greater than about 750:1, or greater than about 1000:1 or more in some cases.

A "nanowire" (e.g. comprising silicon and/or another semiconductor material) is a nanoscopic wire that is typically a solid wire, and may be elongated in some cases. Preferably, a nanowire (which is abbreviated herein as "NW") is an elongated semiconductor, i.e., a nanoscale semiconductor. A "non-nanotube nanowire" is any nanowire that is not a nanotube. In one set of embodiments of the invention, a non-nanotube nanowire having an unmodified surface (not including an auxiliary reaction entity not inherent in the nanotube in the environment in which it is positioned) is used in any arrangement of the invention described herein in which a nanowire or nanotube can be used.

As used herein, a "nanotube" (e.g. a carbon nanotube) is a nanoscopic wire that is hollow, or that has a hollowed-out core, including those nanotubes known to those of ordinary skill in the art. "Nanotube" is abbreviated herein as "NT." Nanotubes are used as one example of small wires for use in the invention and, in certain embodiments, devices of the invention include wires of scale commensurate with nanotubes. Examples of nanotubes that may be used in the present invention include, but are not limited to, single-walled nanotubes (SWNTs). Structurally, SWNTs are formed of a single graphene sheet rolled into a seamless tube. Depending on the diameter and helicity, SWNTs can behave as one-dimensional metals and/or semiconductors. SWNTs. Methods of manufacture of nanotubes, including SWNTs, and characterization are known. Methods of selective functionalization on the ends and/or sides of nanotubes also are known, and the present invention makes use of these capabilities for molecular electronics in certain embodiments. Multi-walled nanotubes are well known, and can be used as well.

As used herein, an "elongated" article (e.g. a semiconductor or a section thereof) is an article for which, at any point along the longitudinal axis of the article, the ratio of the length of the article to the largest width at that point is greater than 2:1.

A "width" of an article, as used herein, is the distance of a straight line from a point on a perimeter of the article, through the center of the article, to another point on the perimeter of the article. As used herein, a "width" or a "cross-sectional dimension" at a point along a longitudinal axis of an article is the distance along a straight line that passes through the center of a cross-section of the article at that point and connects two points on the perimeter of the cross-section. The "cross-section" at a point along the longitudinal axis of an article is a plane at that point that crosses the article and is orthogonal to the longitudinal axis of the article. The "longitudinal axis" of an article is the axis along the largest dimension of the article. Similarly, a "longitudinal section" of an article is a portion of the article along the longitudinal axis of the article that can have any length greater than zero and less than or equal to the length of the article. Additionally, the "length" of an elongated article is a distance along the longitudinal axis from end to end of the article.

As used herein, a "cylindrical" article is an article having an exterior shaped like a cylinder, but does not define or reflect any properties regarding the interior of the article. In other words, a cylindrical article may have a solid interior, may have a hollowed-out interior, etc. Generally, a cross-section of a cylindrical article appears to be circular or approximately circular, but other cross-sectional shapes are also possible, such as a hexagonal shape. The cross-section may have any arbitrary shape, including, but not limited to, square, rectangular, or elliptical. Regular and irregular shapes are also included.

As used herein, an "array" of articles (e.g., nanoscopic wires) comprises a plurality of the articles, for example, a series of aligned nanoscale wires, which may or may not be in contact with each other. As used herein, a "crossed array" or a "crossbar array" is an array where at least one of the articles contacts either another of the articles or a signal node (e.g., an electrode).

The invention provides, in certain embodiments, a nanoscale wire or wires forming part of a system constructed and arranged to determine an analyte in a sample to which the nanoscale wire(s) is exposed. "Determine," in this context, generally refers to the analysis of a species, for example, quantitatively or qualitatively, and/or the detection of the presence or absence of the species. "Determining" may also refer to the analysis of an interaction between two or more species, for example, quantitatively or qualitatively, and/or by detecting the presence or absence of the interaction, e.g. determination of the binding between two species. As an example, an analyte may cause a determinable change in an electrical property of a nanoscale wire (e.g., electrical conductivity, resistivity, impedance, etc.), a change in an optical property of the nanoscale wire, etc. Examples of determination techniques include, but are not limited to, piezoelectric measurement, electrochemical measurement, electromagnetic measurement, photodetection, mechanical measurement, acoustic measurement, gravimetric measurement, and the like. "Determining" also means detecting or quantifying interaction between species.

A "fluid," as used herein, generally refers to a substance that tends to flow and to conform to the outline of its container. Typically, fluids are materials that are unable to withstand a static shear stress. When a shear stress is applied to a fluid, it experiences a continuing and permanent distortion. Typical fluids include liquids and gases, but may also include free-flowing solid particles, viscoelastic fluids, and the like.

As used herein, a component that is "immobilized relative to" another component either is fastened to the other component or is indirectly fastened to the other component, e.g., by being fastened to a third component to which the other component also is fastened. For example, a first entity is immobilized relative to a second entity if a species fastened to the surface of the first entity attaches to an entity, and a species on the surface of the second entity attaches to the same entity, where the entity can be a single entity, a complex entity of multiple species, another particle, etc. In certain embodiments, a component that is immobilized relative to another component is immobilized using bonds that are stable, for example, in solution or suspension. In some embodiments, non-specific binding of a component to another component, where the components may easily separate due to solvent or thermal effects, is not preferred.

As used herein, "fastened to or adapted to be fastened to," as used in the context of a species relative to another species or a species relative to a surface of an article (such as a nanoscale wire), or to a surface of an article relative to another surface, means that the species and/or surfaces are chemically or biochemically linked to or adapted to be linked to, respectively, each other via covalent attachment, attachment via specific biological binding (e.g., biotin/streptavidin), coordinative bonding such as chelate/metal binding, or the like. For example, "fastened" in this context includes multiple chemical linkages, multiple chemical/biological linkages, etc., including, but not limited to, a binding species such as a peptide synthesized on a nanoscale wire, a binding species specifically biologically coupled to an antibody which is bound to a protein such as protein A, which is attached to a nanoscale wire, a binding species that forms a part of a molecule, which in turn is specifically biologically bound to a binding partner covalently fastened to a surface of a nanoscale wire, etc. A species also is adapted to be fastened to a surface if a surface carries a particular nucleotide sequence, and the species includes a complementary nucleotide sequence.

"Specifically fastened" or "adapted to be specifically fastened" means a species is chemically or biochemically linked to or adapted to be linked to, respectively, another specimen or to a surface as described above with respect to the definition of "fastened to or adapted to be fastened," but excluding essentially all non-specific binding. "Covalently fastened" means fastened via essentially nothing other than one or more covalent bonds.

The term "binding" refers to the interaction between a corresponding pair of molecules or surfaces that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones and the like. Specific non-limiting examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, virus/cell surface receptor, etc.

The term "binding partner" refers to a molecule that can undergo binding with a particular molecule. Biological binding partners are examples. For example, Protein A is a binding partner of the biological molecule IgG, and vice versa. Other non-limiting examples include nucleic acid-nucleic acid binding, nucleic acid-protein binding, protein-protein binding, enzyme-substrate binding, receptor-ligand binding, receptor-hormone binding, antibody-antigen binding, etc. Binding partners include specific, semi-specific, and non-specific binding partners as known to those of ordinary skill in the art. For example, Protein A is usually regarded as a "non-specific" or semi-specific binder. The term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair the ligand would specifically and/or preferentially select its receptor from a complex mixture of molecules, or vice versa. An enzyme would specifically bind to its substrate, a nucleic acid would specifically bind to its complement, an antibody would specifically bind to its antigen. Other examples include nucleic acids that specifically bind (hybridize) to their complement, antibodies specifically bind to their antigen, binding pairs such as those described above, and the like. The binding may be by one or more of a variety of mechanisms including, but not limited to ionic interactions, and/or covalent interactions, and/or hydrophobic interactions, and/or van der Waals interactions, etc.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

As used herein, terms such as "polynucleotide" or "oligonucleotide" or grammatical equivalents generally refer to a polymer of at least two nucleotide bases covalently linked together, which may include, for example, but not limited to, natural nucleosides (e.g., adenosine, thymidine, guanosine, cytidine, uridine, deoxyadenosine, deoxythymidine, deoxyguanosine and deoxycytidine), nucleoside analogs (e.g., 2-aminoadenosine, 2-thiothymidine, inosine, pyrrolopyrimidine, 3-methyladenosine, C5-bromouridine, C5-fluorouridine, C5-iodouridine, C5-propynyluridine, C5-propynylcytidine, C5-methylcytidine, 7-deazaadenosine, 7-deazaguanosine, 8-oxoadenosine, 8-oxoguanosine, O6-methylguanosine, 2-thiocytidine, 2-aminopurine, 2-amino-6-chloropurine, 2,6-diaminopurine, hypoxanthine), chemically or biologically modified bases (e.g., methylated bases), intercalated bases, modified sugars (2'-fluororibose, arabinose, or hexose), modified phosphate moieties (e.g., phosphorothioates or 5'-N-phosphoramidite linkages), and/or other naturally and non-naturally occurring bases substitutable into the polymer, including substituted and unsubstituted aromatic moieties. Other suitable base and/or polymer modifications are well-known to those of skill in the art. Typically, an "oligonucleotide" is a polymer having 20 bases or less, and a "polynucleotide" is a polymer having at least 20 bases. Those of ordinary skill in the art will recognize that these terms are not precisely defined in terms of the number of bases present within the polymer strand.

A "nucleic acid," as used herein, is given its ordinary meaning as used in the art. Nucleic acids can be single-stranded or double stranded, and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp. 169-176). Several nucleic acid analogs are described in Rawls, Chemical & Engineering News, Jun. 2, 1997 page 35. These modifications of the ribose-phosphate backbone may be done to facilitate the addition of additional moieties such as labels, or to increase the stability and half-life of such molecules in physiological environments.

As used herein, an "antibody" refers to a protein or glycoprotein including one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well characterized fragments produced by digestion with various peptidases. Thus, for example, pepsin digests an antibody below (i.e. toward the Fc domain) the disulfide linkages in the hinge region to produce F(ab)'2, a dimer of Fab which itself is a light chain joined to $V_H$-$C_H1$ by a disulfide bond. The F(ab)'2 may be reduced under mild conditions to break the disulfide linkage in the hinge region thereby converting the (Fab')$_2$ dimer into an Fab' monomer. The Fab' monomer is essentially a Fab with part of the hinge region (see, Paul (1993) *Fundamental Immunology*, Raven Press, N.Y. for a more detailed description of other antibody fragments). While various antibody fragments are defined in terms of the digestion of an intact antibody, one of skill will appreciate that such fragments may be synthesized de novo either chemically, by utilizing recombinant DNA methodology, or by "phage display" methods (see, e.g., Vaughan et al. (1996) *Nature Biotechnology*, 14(3): 309-314, and PCT/US96/10287). Preferred antibodies include single chain antibodies, e.g., single chain Fv (scFv) antibodies in which a variable heavy and a variable light chain are joined together (directly or through a peptide linker) to form a continuous polypeptide.

The term "quantum dot" is known to those of ordinary skill in the art, and generally refers to semiconductor or metal nanoparticles that absorb light and quickly re-emit light in a different color depending on the size of the dot. For example, a 2 nanometer quantum dot emits green light, while a 5 nanometer quantum dot emits red light. Cadmium selenide quantum dot nanocrystals are available from Quantum Dot Corporation of Hayward, Calif.

The following documents are incorporated herein by reference in their entirety for all purposes, and include additional description of teachings usable with the present invention: U.S. patent application Ser. No. 09/935,776, filed Aug. 22, 2001, entitled "Doped Elongated Semiconductors, Growing Such Semiconductors, Devices Including Such Semiconductors, and Fabricating Such Devices," by Lieber, et al., published as U.S. Patent Application Publication No. 2002/0130311 on Sep. 19, 2002; U.S. patent application Ser. No. 10/033,369, filed Oct. 24, 2001, entitled "Nanoscopic Wire-Based Devices and Arrays," by Lieber, et al., published as U.S. Patent Application Publication No. 2002/0130353 on Sep. 19, 2002, now U.S. Pat. No. 6,781,166, issued Aug. 24, 2004; U.S. patent application Ser. No. 10/020,004, filed Dec. 11, 2001, entitled "Nanosensors," by Lieber, et al., published as U.S. Patent Application Publication No. 2002/0117659 on Aug. 29, 2002; U.S. patent application Ser. No. 10/152,490, filed May 20, 2002, entitled "Nanoscale Wires and Related Devices," by Lieber, et al.; U.S. patent application Ser. No. 10/196,337, filed Jul. 16, 2002, entitled "Nanoscale Wires and Related Devices," by Lieber, et al., published as U.S. Patent Application Publication No. 2003/0089899 on May 15, 2003; U.S. patent application Ser. No. 10/720,020, filed Nov. 21, 2003, entitled "Nanoscale Wires and Related Devices," by Lieber, et al., published as U.S. Patent Application Publication No. 2003/0089899 on May 15, 2003; U.S. patent application Ser. No. 10/812,653, filed Mar. 29, 2004, entitled "Nanoscopic Wire-Based Devices and Arrays," by Lieber, et al., published as U.S. Patent Application Publication No. 2004/0188721 on Sep. 30, 2004; U.S. patent application Ser. No. 10/973,665, filed Oct. 26, 2004, entitled "Nanoscopic Wire-Based Devices and Arrays," by Lieber, et al., published as U.S. Patent Application Publication No. 2005/0117441 on Jun. 2, 2005; U.S. patent application Ser. No. 10/995,075, filed Nov. 22, 2004, entitled "Nanoscale Arrays and Related Devices," by Whang, et al., published as U.S. Patent Application Publication No. 2005/0253137 on Nov. 17, 2005; U.S. patent application Ser. No. 11/058,443, filed Feb. 14, 2005, entitled "Nanoscale Wires and Related Devices," by Lieber, et al.; International Patent Application No. PCT/US2005/004459, filed Feb. 14, 2005, entitled "Nanostructures Containing Metal-Semiconductor Compounds," by Lieber, et al., published as WO 2005/093831 on Oct. 6, 2005; U.S. patent application Ser. No. 11/137,784, filed May 25, 2005, entitled "Nanoscale Sensors," by Lieber, et al.; U.S. Provisional Patent Application Ser. No. 60/707,136, filed Aug. 9, 2005, entitled "Nanoscale Sensors," by Lieber, et al.; U.S. Provisional Patent Application Ser. No. 60/790,322, filed Apr. 7, 2006, entitled "Nanoscale Wire Methods and Devices," by Lieber, et al.; U.S. Provisional Patent Application Ser. No. 60/812,884, filed Jun. 12, 2006, entitled "Nanosensors and Related Technologies," by Lieber, et al.; and U.S. patent application Ser. No. 11/501,466, filed Aug. 9, 2006, entitled "Nanoscale Sensors," by Lieber, et al. Also incorporated herein by reference is U.S. Provisional Patent Application Ser. No. 60/860,586, filed Nov. 22, 2006, entitled "High-Sensitivity Nanowire Sensors," by Lieber, et al.

The following examples are intended to illustrate certain embodiments of the present invention, but do not exemplify the full scope of the invention.

Example 1

In this example, the sensitivity of a nanowire (NW) field effect transistor (FET) sensor prepared in accordance with one embodiment of the invention is shown to be enhanced in the low carrier concentration regime where the screening length is longer than the radius of the nanowire, and therefore the molecules bound on surface can gate the whole cross-section of nanowire. This is shown by operating a Si-NW FET biosensor in the subthreshold regime with the devices gated in electrolyte. It was shown that the NW FET biosensor operating in the subthreshold regime had high charge sensitivity and a high percentage change in conductance response, which may depend exponentially on the surface potential shift induced by the binding of analyte molecules. This example also shows that optimization of a nanowire FET structure and operating conditions can provide a significant enhancement of, as well as a fundamental understanding for, the sensitivity of a NW-FET sensor. For example, operating in the subthreshold regime was shown in this example to improve the prostate specific antigen (PSA) detection limit down to ~1.5 fM for a NW-FET sensor with a ~0.75 pM detection limit in the linear regime. Also, it may be possible to detect down to as small as several electron charges with the NW FET sensors working in the subthreshold regime, as is shown in this example. These results may have general implications on the sensitivity limits of other FET sensors as well.

For NW biosensors operated as FETs, the sensing mechanism is the field gating effect of charged molecules on the carrier conduction inside NW. Therefore, the highest sensitivity may be achieved when the whole volume of nanodevice is gated by surface charges. This situation may be realized when the carrier screening length is much larger than the radius of the NW, R. Conductance changes of NW FETs can be used to detect pH, proteins, and viruses, for example, as is discussed in U.S. patent application Ser. No. 11/501,466, filed Aug. 9, 2006, entitled "Nanoscale Sensors," by Lieber, et al., incorporated herein by reference.

Si-NWs used for sensor application often have R on the order of 100 nm, or 10 nm in some cases. In most cases, charged molecules bound on the surface gate the NW within a surface layer of thickness ~1-2 nm. However, at much lower hole densities, p (e.g., lower than $10^{18}/cm^3$), $\lambda_{Si} \gg R$ and the whole volume of the NW may be gated by molecules at surface. Thus, there may be a greater response of device and/or an increase in sensor sensitivity under these conditions.

A schematic comparison between these two scenarios is shown in FIG. 1, together with the screening length in silicon plotted as a function of p. This figure shows the screening length effect on the operation and sensitivity of NW FET sensors. The working regime and effectiveness of gating effect induced by molecules at the surface of the NW-FET sensors were determined by the relative magnitude between carrier screening length $\lambda_{Si}$ and nanowire size (radius) R. In the high carrier concentration regime where $\lambda_{Si} \ll R$, NW-FET works in the linear regime, where the conductance G varies with gate voltage linearly. In the low carrier concentration regime where $\lambda_{Si} \gg R$, NW-FET works in the depletion (subthreshold) regime, where G varies with gate voltage exponentially. In the linear regime, the field effect of positive/negative surface charges induced band bending and carrier depletion/enhancement inside the NW within a region of depth $\sim_{Si}$. The amount of band bending at the NW surface is also denoted as surface potential shift $\Delta\phi_{Si}$. In the subthreshold (depletion) regime, carriers in the NW may have long screening length ($\lambda_{Si} \gg r$) and the field effect of surface charges can gate the whole NW, fully utilizing the high surface volume ratio of NW. In this case, the Fermi level $E_F$ is shifted by $\Delta\phi_{Si}$, relative to the band edges throughout the whole cross-section of NW.

Figure 5:
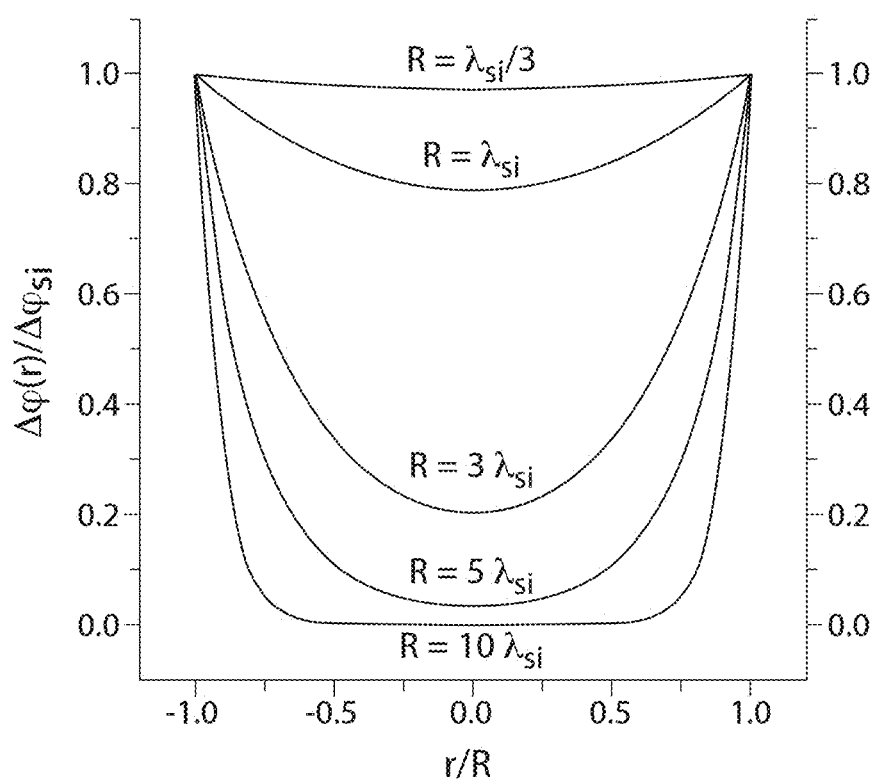
FIG. 5 shows the potential distribution of a nanoscale wire, according to yet another embodiment of the invention.

By solving the Poisson equation in cylindrical coordinates, one can find the distributions of electrostatic potential $\Delta\phi(r)$ and carrier density change $\Delta p(r)$ inside a NW for a given surface potential change $\Delta\phi_{Si}$ induced by binding of biomolecules. Calculations show that once the Debye screening length of silicon $\lambda_{Si}$, ($=\sqrt{\in_{Si} k_B T/pe^2}$) becomes 2-3 times longer than R, $\Delta\phi(r) \sim \Delta\phi_{Si}$ throughout the radial direction, and the whole cross-section of the NW is gated by surface charges (FIG. 5). The hole (or other majority carrier) density depends on the Fermi energy $E_F$ as $p=p_i\times\exp(E_i-E_F/k_B T)$ ($p_i$ and $E_i$ are the hole density and Fermi energy for an intrinsic semiconductor); thus, the surface charge gating effect may cause an almost uniform hole density change $\Delta p(r)=p\times\exp(-e\Delta\phi_{Si}/k_B T)$ throughout the radial direction of NW if $\lambda_{Si} \gg R$ at low carrier density and/or at small NW radius. The conductance change of NW device in this case is $$\Delta G = e\mu \int_0^R 2\pi r \Delta p \, dr = e\mu \times \pi R^2 \times p \times \{\exp(-e\Delta\varphi_{Si}/k_B T) - 1\}.$$

It should be noted that although $\Delta G$, the conductance change of device, is the direct readout measured in the sensing experiments, it is more useful in some instances to characterize the intrinsic sensitivity of the NW FET sensor by $\Delta G/G$, the percentage in the conductance change. Using $\Delta G/G$ to study the sensitivity has a physically meaningful motivation: it is related to the volume ratio between the part of NW that is gated by surface charges (represented by $\Delta G$) and the whole body of NW (represented by G). Therefore, $\Delta G/G$ is expected to reach maximum when the surface/volume of nanosensor is fully utilized, which happens when the sensor is near carrier depletion, such that the carrier density is low and $\lambda_{Si} \gg R$. Using the above expression for $\Delta G$ and $G=e\times\mu\times p\times\pi R^2$ yields the relative conductance response for NW FET sensors in the regime with highest sensitivity ($\lambda_{Si} \gg R$) as:

$$\Delta G/G = \exp(-e\Delta\phi_{Si}/k_B T) - 1. \quad (1)$$

Although the NW is treated as a three dimensional (3D) system in this derivation, the general approach remains valid when radial confinement makes the system one dimensional (1D), since it only relies on the thermally activated nature of carriers, which follow Boltzmann statistics.

pH sensing experiments were used as a model system to study the sensitivity of NW sensor in the various regimes. Following are nanowire FET fabrication and surface modification for sensing experiments procedures.

Nanowire FET fabrication and electrolyte gating were performed as follows. Silicon nanowires were synthesized by chemical vapor deposition using 10 nm gold nanoparticles as catalysts, with silane as the reactant. Diborane was used during the growth to provide boron as the p-type dopant with a typical B:Si ratio of 1:8000. The FETs were fabricated by photolithography into a patterned array. Nickel (60 nm thick) metal was used as contacts which were passivated/protected from electrolyte by deposition of ~50 nm thick $Si_3N_4$ after nickel evaporation. The distance between the source-drain electrodes for each FET was 2 μm. pH and PSA samples were delivered to the nanowire devices by a microfluidic channel (with a 500 μm width by 50 μm height cross-section) made of flexible PDMS polymer channel sealed to the device chip. The samples were delivered through inlet/outlet connections in the PDMS polymer by a syringe pump running at typical speed of 0.3 ml/hr. A gold metal pad (without $Si_3N_4$ passivation) on the chip was used as a global gate electrode for gating all the devices in electrolyte. The FET conductance was measured by a lock-in amplifier at a frequency of 17 Hz and biased voltage of 30 mV.

Nanowire surface modifications were performed as follows. For pH sensing, the silicon nanowire surface was modified with 3-aminopropyltriethoxysilane (3APTS) to provide amino groups at the nanowire surface. The chip was first reacted with 1% 3APTS in ethanol for ~30 min. Then the chip was rinsed with ethanol and baked at 110° C. for 5-10 min before conductance measurements. For PSA sensing (see below), a two-step modification process was used to link antibody receptors to nanowire. Aldehyde groups were first linked to the NW surface by reacting with 1% 3-(trimethoxysilyl)propyl aldehyde (United Chemical Technologies) in ethanol for ~30 min followed by rinsing with ethanol and baking at 110° C. for 10 min Anti-PSA (AbI, clone ER-PR8, NeoMarkers) was couple to the aldehyde-terminated nanowire surface by reaction of 100 μg/ml antibody in a pH 8.4, 10 mM phosphate buffer solution with 4 mM sodium cyanoborohydride for ~2 h.

Figure 2A:
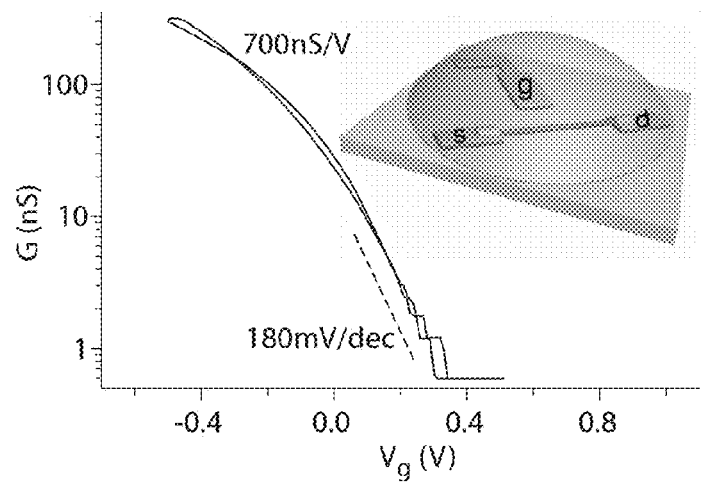
FIGS. 2A-2D illustrates pH sensing, according to another embodiment of the invention.

In the pH sensing experiments, the silicon oxide ($SiO_2$) surface of boron doped p-type Si-NW was modified with 3-aminopropyltriethoxysilane. The protonation/deprotonation of amino (—$NH_2$) and silanol (Si—OH) groups changes the surface charge and surface potential of the NW when the pH of electrolyte solution was varied. A gold pad on the chip was used as a gate electrode to gate the NW-FET devices in the electrolyte (inset, FIG. 2A). FIG. 2A shows the conductance G vs. the electrolyte gate voltage $V_g$ of a p-type NW FET. The inset shows a schematic diagram of electrolyte gating. This device has a transconductance ~700 nS/V in the linear regime and a subthreshold slope S~180 mV/decade in the subthreshold regime, with a threshold voltage $V_T \sim 0$ V.

By setting a voltage $V_g$ on gate electrode, a voltage difference $V_g$ was established between the bulk solution and the NW, and the hole concentration in the NW could be tuned. Typically, the devices in this example could be turned on/off within $V_g = \pm 0.5$V. FIG. 2A shows the $G(V_g)$ curve on a semi-log scale for a NW device with R=5 nm in a pH=7, 10 mM phosphate solution. From the analysis of the NW conductance on surface potential, it can be inferred that the $\lambda_{Si} \gg R$ regime was reached in the $G(V_g)$ plot where G depends exponentially on the electrolyte gate voltage $V_g$, which is called the "subthreshold regime" in semiconductor device physics terminology. The parameter characterizing the FET performance in the subthreshold regime was the subthreshold slope S, which equals the change in $V_g$ needed to tune the device conductance G by a factor of about ten. One can obtain the gate coupling efficiency α by dividing the ideal subthreshold swing at room temperature 60 mV/decade with the measured S. For the device in FIG. 2A, S=180 mV/decade and α=⅓. For the same device, a transconductance $g_m = dG/dV_g \sim 700$ nS/V was determined at $V_g$ less than the threshold voltage $V_T$ (~0 V for this device), where G depended on $V_g$ linearly (the "linear regime" of FET).

Figure 2B:
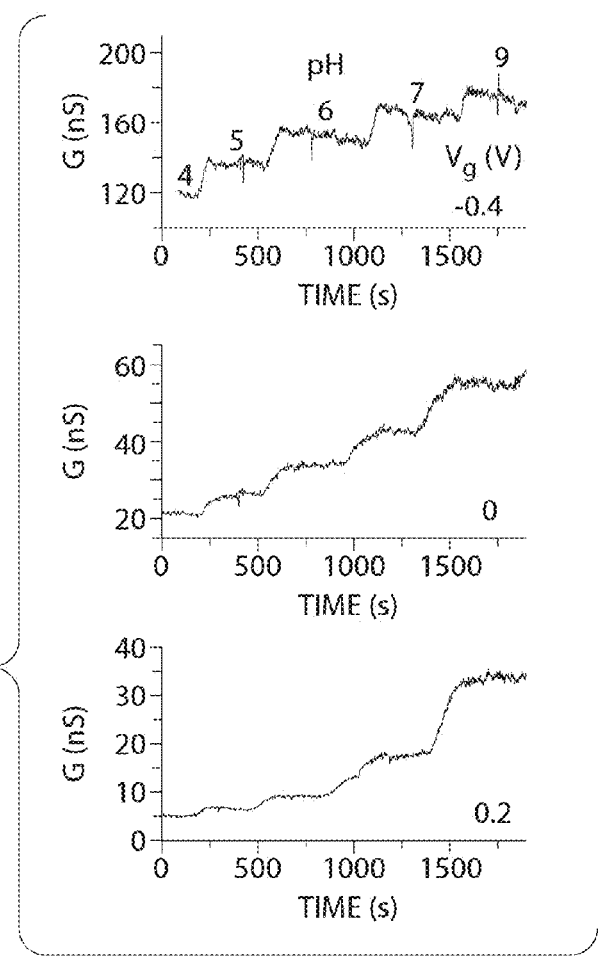
Figure 2C:
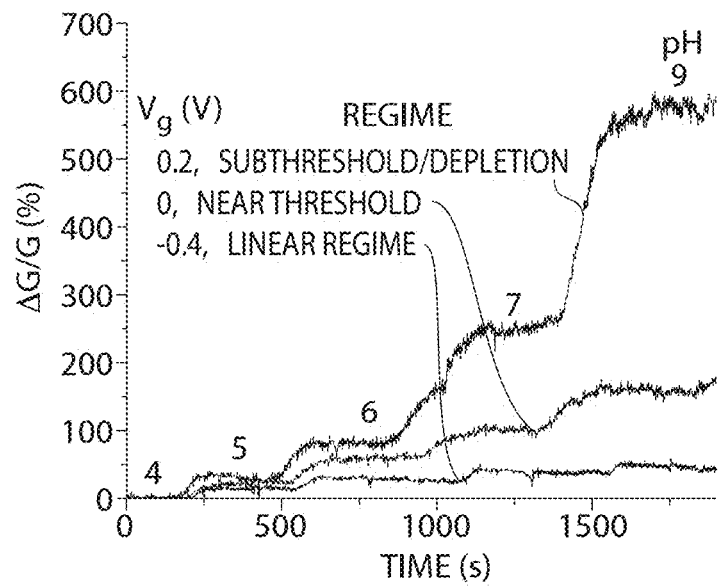

FIG. 2B shows that the conductance versus time data as 10 mM phosphate solutions with pH from 4 to 9 were sequentially delivered into the microfluidic channel where the NW sensors resided. Three sets of data are shown at $V_g = -0.4$ V, 0 V, and 0.2V, at which the device was in the linear, near threshold and subthreshold, regimes, respectively. At higher pH, deprotonation of amino and silanol groups at the modified $SiO_2$ surface made the NW surface more negatively charged, inducing a negative surface potential at NW surface and enhancing the conductance of p-type NW. It is important to note that in FIG. 2B, while G increased with pH quasi-linearly at $V_g$=−0.4 V, G had a much stronger dependence on pH at $V_g$=+0.2 V, which was in the subthreshold regime. This feature can be seen in comparison to the data in terms of relative conductance change, $\Delta G/G$=G−G(pH=4)/G(pH=4), as shown in FIG. 2C. As discussed above, $\Delta G/G$ may be related to the how well the surface/volume ratio of NW is utilized and may increase greatly in the subthreshold regime. Indeed, FIG. 2C shows that from pH=4 to 9, $\Delta G/G$ increased from ~50% at $V_g$=−0.4 V to nearly 600% at $V_g$=0.2V, more than an order of magnitude enhancement. The real time pH sensing data in FIG. 2B are plotted in this figure as the percentage change, $\Delta G/G$, with the conductance value at pH=4 as reference point. In the subthreshold regime ($V_g$=+0.2V), the device shows much larger percentage change in conductance as solution pH changes.

Figure 2D:
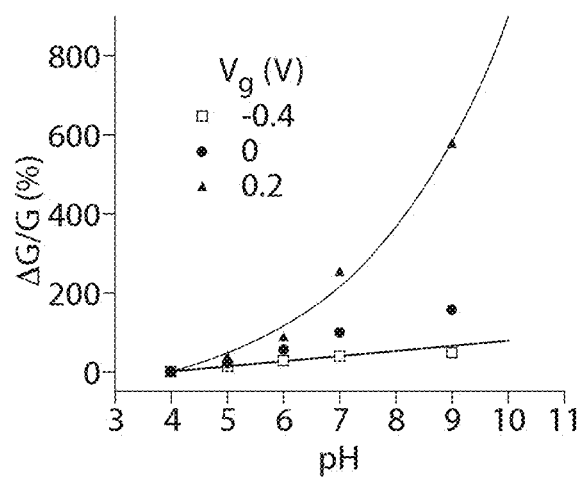

The response of the NW pH sensor was further analyzed at different $V_g$'s by plotting $\Delta G/G$ as a function of pH in FIG. 2D, which shows device conductance as a function of pH value at $V_g$=−0.4, 0 and +0.2V. The upper and lower lines in this figure are exponential and linear responses for pH induced surface potential shift of −30 mV/pH. Since in experiments, the potential at the SiO$_2$ surface was measured instead of the potential at the Si/SiO$_2$ interface of NW, the data were analyzed in terms of $\Delta\phi_{SiO2}$, the surface potential at the SiO$_2$/electrolyte interface. The $\Delta G/G$ data at $V_g$=−0.4 V were fitted to a linear dependence: $\Delta G/G$(pH=4)=$g_m$× $\Delta\phi_{SiO2}/G$(pH=4) with $\Delta\phi_{SiO2}$ as the only fitting parameter. Using $g_m$=700 nS/V obtained from the G($V_g$) data in electrolyte-gating measurement, $\Delta\phi_{SiO2}$≈−30 mV/pH was obtained. The negative sign comes from the fact that the SiO$_2$ surface is more negatively charged at higher pH. Below, the pH sensing data were analyzed in the subthreshold regime according to the analysis on the NW sensor response in the $\lambda_{Si}$>>R regime. To take into account of the potential drop inside SiO$_2$ layer and the gate coupling efficiency, Eq. 1 was modified to:

$$\Delta G/G = \exp(-\alpha e\Delta\phi_{SiO2}/k_BT)-1. \quad (2)$$

Fitting the $V_g$=+0.2V data in FIG. 2D to Eq. 2 with the gate coupling efficiency $\alpha$=⅓, $\Delta\phi_{SiO2}$≈−30 mV/pH was obtained, consistent with the value in the linear regime. The pH sensitivity in terms of surface potential of materials had a theoretical limit of 60 mV/pH, which is set by the Nernst equation. Depending on site densities and the dissociation constants of functional groups on the material surface, the measured $\Delta\phi$(pH) may be lower than the ideal 60 mV/pH.

Example 2

An important advantage of the sensors described herein is their relatively high sensitivity, which may allow purely electrical methods to be used to study analytes such as single biomolecules. This example gives a quantitative calculation of the detected surface charge for a NW sensor with cylindrical geometry, and shows that the subthreshold regime has a low charge detection limit for FET nanosensors. The charge detected for surface potential $\Delta\phi_{SiO2}$ at the SiO$_2$/electrolyte interface is given by Q=C×$\Delta\phi_{SiO2}$, where C is the capacitance between the surface charge and the NW/electrolyte system. In calculating C, there are three capacitances: the double layer (DL) capacitance $C_{DL}$, the SiO$_2$ layer capacitance $C_{ox}$, and the capacitance of charging NW $C_{NW}$. When there are surface charges at the SiO$_2$ surface, carriers in the NW and counter-ions in the electrolyte will come close to the SiO$_2$ surface to screen out the surface charge. Since surface charge of SiO$_2$ equals to the net charge in NW plus the charge in the DL of the electrolyte, C can be modeled as $C_{DL}$ in parallel with the series capacitance of $C_{ox}$ and $C_{NW}$:

$$C=(1/C_{ox}+1/C_{NW})^{-1}+C_{DL}. \quad (3)$$

Using the double cylinder capacitance formula $2\pi\epsilon_{SiO2}$/ln(1+d/R), $C_{ox}$=1.4×10$^{-15}$ F/μm for a typical Si-NW with native SiO$_2$ thickness d~1 nm and R=5 nm. The capacitance of the NW, $C_{NW}$, characterizes how much the chemical potential (or the Fermi energy $E_F$) of the carriers shifts with respect to the carrier density change: $C_{NW}$=e$^2$dp/d$E_F$. For non-degenerate carriers in NW, the following is derived: $C_{NW}$≈e$^2$×p×2πR$\lambda_{Si}/k_BT$ for $\lambda_{Si}$<<R, and $C_{NW}$≈e$^2$×p×πR$^2$/$k_BT$ for $\lambda_{Si}$>>R (see below). Note that $C_{NW}$ decreased quickly as the NW was gated from the linear to the subthreshold regime. For instance, $C_{NW}$ drops from ~3×10$^{-15}$ F/μm to ~5×10$^{-18}$ F/μm as p decreased from 1×10$^{19}$/cm$^3$ ($\lambda_{Si}$~1.5 nm) to 1×10$^{16}$/cm$^3$ ($\lambda_{Si}$~35 nm). Therefore, in the high p limit, C~$C_{ox}$+$C_{DL}$ and in the low p limit, C~$C_{DL}$. By solving the spatial potential distribution inside DL for cylindrical coordinates, the NW-electrolyte DL capacitance was calculated to be $C_{DL}$=π$\epsilon$×K$_1$(x)/K$_0$(x) (see below), where $\epsilon$=80 is the dielectric constant of water, x=R/λ with λ as the Debye-Huckel screening length of the electrolyte, and K$_0$(x) and K$_1$(x) are the zero and first order modified Bessel functions of the second kind. For a 10 mM KCl solution, λ~3 nm and R=5 nm, $C_{DL}$≈4.7×10$^{-15}$ F/μm. For these parameters, the 2 μm long NW-sensor was estimated to detect $\Delta Q$ ($C_{ox}$+$C_{DL}$)×30 mV/pH=2300 e/pH in the linear regime, and $\Delta Q$~$C_{DL}$×30 mV/pH=1800 e/pH in the subthreshold regime (e being the elementary charge).

From the above discussion, it can be seen that lower charge detection limit $\Delta Q_{min}$, of the NW sensors could be obtained by reducing $C_{NW}$ and $C_{DL}$. Thus, better charge sensitivity could be obtained in the subthreshold regime (where $C_{NW}$→0) and in electrolyte with small ionic strength I (as λ∝I$^{-1/2}$). In Table 1, $\Delta Q_{min}$=C$\Delta\phi_{min}$ is listed for the sensor shown in FIG. 2. Here, the minimal detectable surface potential shift $\Delta\phi_{min}$~5 mV and 0.67 mV in the linear and subthreshold regimes respectively. Also shown are the corresponding $\Delta Q_{min}$, assuming a low ionic strength I=10 μM were used. Table 1 shows that it is possible to detect charge as little as several e using a NW FET sensor working in the subthreshold regime and low ionic strength electrolyte. Besides demonstrating, in this example, the capability of NW FET devices as sensitive charge sensors, these quantitative determinations also provide a fundamental understandings for charge sensitivity of a nanosensor made from quasi-1D materials.

TABLE 1

Estimated surface charge detection limit $\Delta Q_{min}$ = C$\Delta\phi_{min}$
(in units of elementary electron charge e) per μm long silicon NW
FET sensor in 10 mM or 10 μM solutions

|  | Linear regime $\Delta Q_{min}$~($C_{ox}$ + $C_{DL}$)$\Delta\phi_{min}$ | Subthreshold regime $\Delta Q_{min}$~$C_{DL}$ $\Delta\phi_{min}$ |
|---|---|---|
| $\Delta Q_{min}$/μm at I = 10 mM | 200 e | 20 e |
| $\Delta Q_{min}$/μm at I = 10 μM | 70 e | 3 e |

Example 3

Figure 3A:
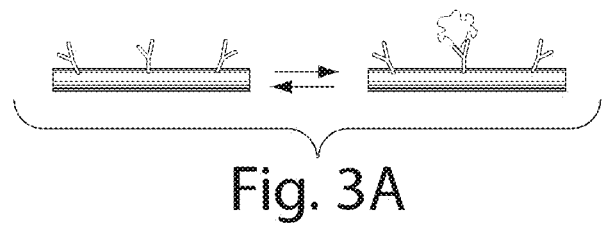
FIGS. 3A-3D illustrates sensing of PSA/antibody conjugates, in yet another embodiment of the invention.

Besides sensing simple chemical ions, NW sensors can also be used in high throughput sensitive detection of complex biomolecules such as proteins. This example is a demonstration of biomolecule detection in the subthreshold regime of the NW sensor for a cancer marker protein, prostate specific antigen (PSA). As discussed above, for PSA detection, a p-type Si-NW surface was first modified with aldehyde propyltrimethoxysilane, which provides aldehyde groups at NW surface. The aldehyde terminated NW surface was then covalently linked with PSA antibodies, which act as receptors to detect the PSA molecules in analyte solutions, as shown in FIG. 3A, which is a schematic of the PSA/PSA-Ab binding/unbinding equilibrium system.

Figure 3B:
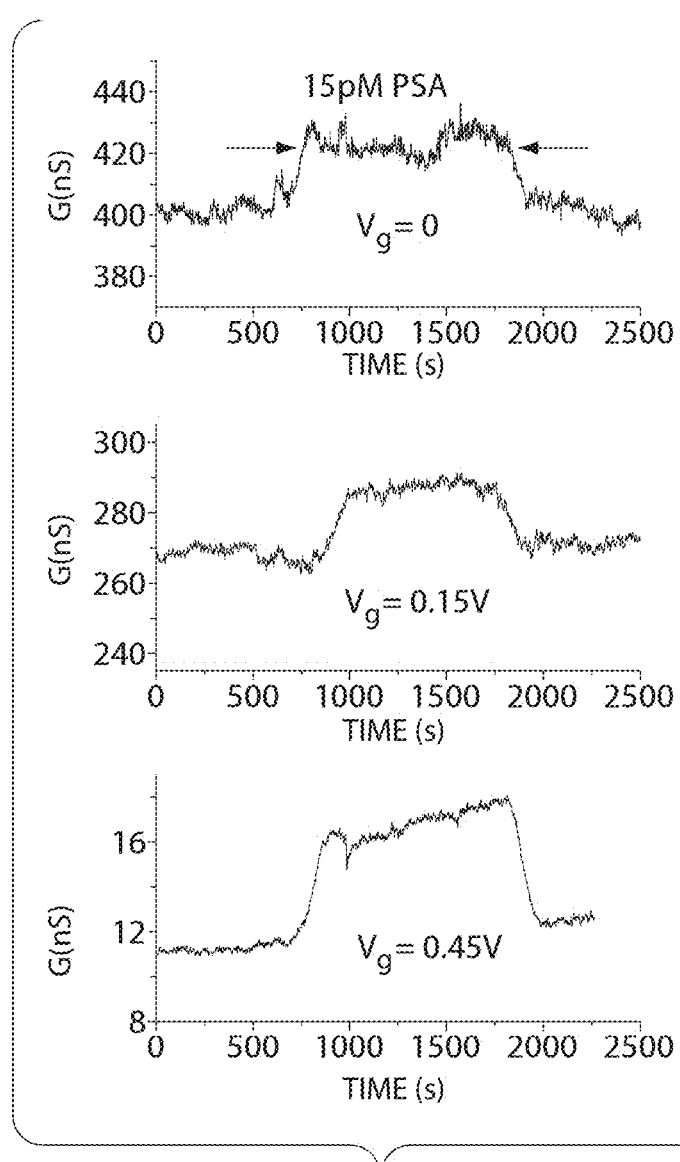

The PSA-antibody molecules were first linked to nanowire surface. When there are PSA molecules present in sample solution, some antibody sites will be occupied by PSA. The binding of charged PSA molecules thus may induce a field gating effect, which can change the device conductance. FIG. 3B presents data on detecting 15 pM PSA at different electrolyte gate voltage $V_g$. The 15 pM PSA sample and buffer solution were sequentially delivered. This device was operated in the linear regime at $V_g=0$ and in the subthreshold regime at $V_g=0.45$ V. FIG. 3B also shows data at the electrolyte gate voltage $V_g=0$ V, 0.15 V, and 0.45 V. The increased conductance between the arrows was caused by the binding of negatively charged PSA molecules on the p-type NW surface. A low ionic strength solution (10 μM potassium phosphate+10 μM KCl, pH~7.4) was used in the PSA sensing experiments to enhance sensitivity. Since PSA molecules have an isoelectric point of ~pH=6.8, and were negatively charged at pH=7.4, the p-type NW FET device conductance increased when the PSA bound to the antibodies.

Figure 3C:
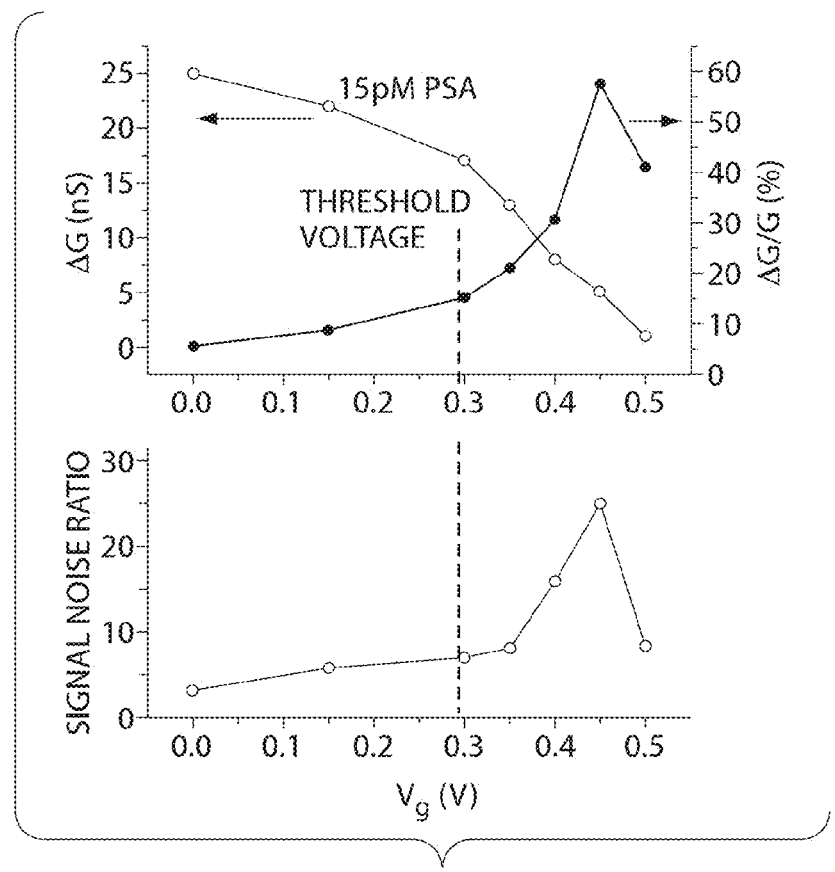
Figure 3D:
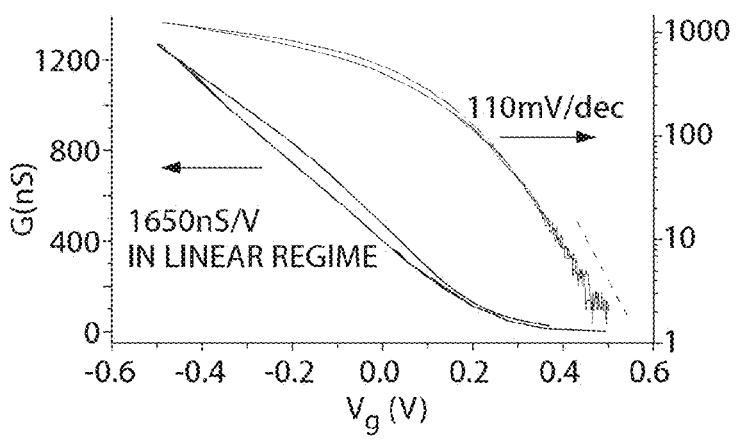

In FIG. 3B, it can be seen that the 15 pM PSA was more readily detected at $V_g=0.45$ V. The absolute conductance change ΔG and relative conductance change ΔG/G for the binding/unbinding signal of 15 pM PSA sample are plotted in the upper panel of FIG. 3C as a function of $V_g$. The percentage change in conductance increased rapidly as the device was gated into the subthreshold regime, despite a decreasing ΔG. Similar to the analysis on pH sensing, $\Delta\phi_{SiO2}=\Delta G/g_m\sim-15$ mV for detecting 15 pM PSA in the linear regime, with $g_m=1650$ nS/V extracted from the conductance vs. electrolyte gate voltage data with G in linear (left) or log(right) scale (FIG. 3D).

$\Delta\phi_{SiO2}$ was determined in the subthreshold regime as follows. Similar to the pH sensing analysis, $\Delta G/G=\exp(-\alpha e \Delta\phi_{SiO2}/k_BT)-1$ in the subthreshold regime, with $\alpha=0.55$ calculated from the subthreshold slope S=110 mV/decade for this device. In the subthreshold regime, ΔG/G ~50%, indicating $\Delta\phi_{SiO2}\sim-19$ mV. This value was close to the value in the linear regime. Another practically useful parameter in sensing experiments is the signal to noise ratio, which also increased in the subthreshold regime, as displayed in the lower panel of FIG. 3C. However, although ΔG showed some decrease in the subthreshold regime, the conductance noise in the NW FET dropped more rapidly, giving rise to a better signal to noise ratio. Further detailed study showed that the NW FET conductance noise was the dominant noise source in these experiments (except when the device is completely turned off) and the conductance noise originated from mobility fluctuations so that the noise was proportional to carrier density in the device and decreased significantly in the subthreshold regime. The much smaller conductance noise in the subthreshold regime was visible in the raw data in FIG. 3B. Furthermore, performing sensing with the device completely gated off made both ΔG/G and signal to noise ratio decrease, as shown by the data point for $V_g=+0.5$V in FIG. 3C. It is believed that the conductance measurement and noise level in this regime were dominated by current leakage between the device and the electrolyte. It can thus be concluded that for protein detection, the sensor performance may also be relatively optimized (in terms of the highest ΔG/G and signal to noise ratio) in the subthreshold regime, consistent with the above discussion based on the screening length effect on the sensitivity as well as the pH sensing experiments.

Figure 4A:
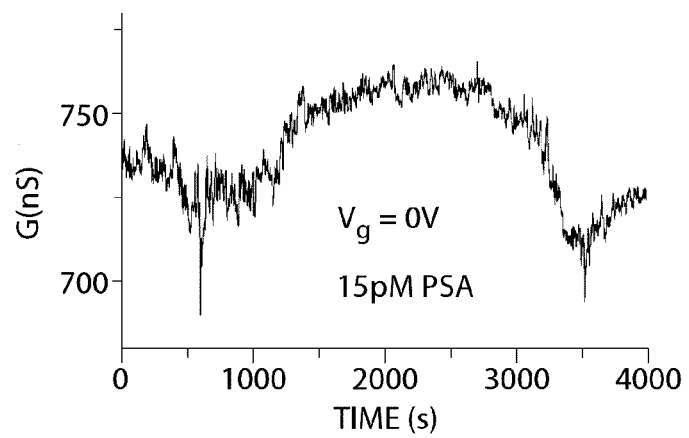
FIGS. 4A-4F illustrate sensing of PSA/antibody conjugates, in still another embodiment of the invention.
Figure 4B:
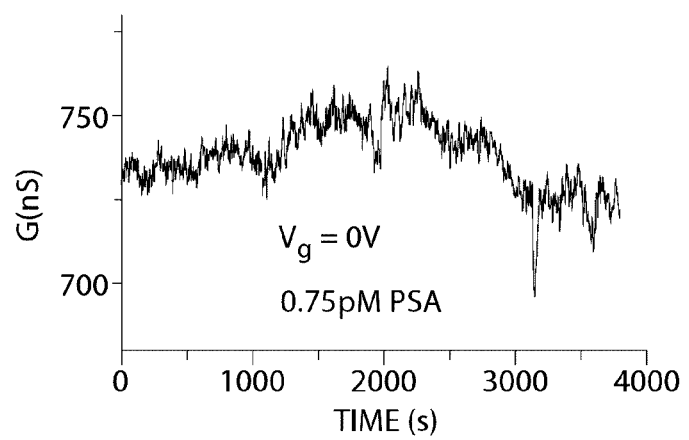
Figure 4C:
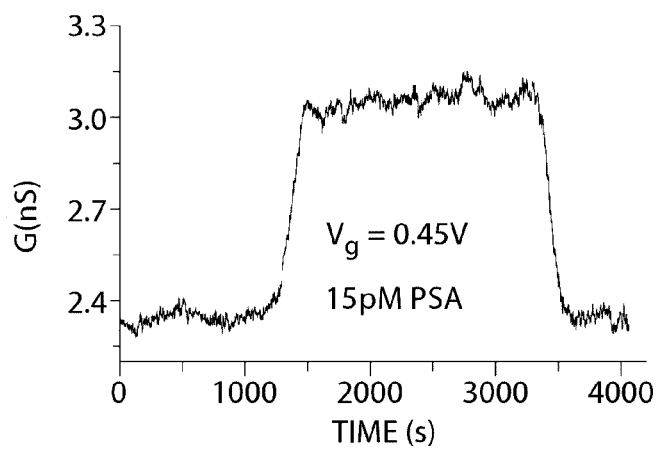
Figure 4D:
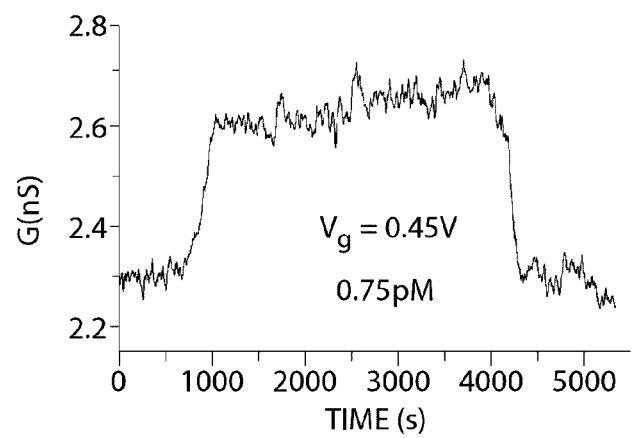
Figure 4E:
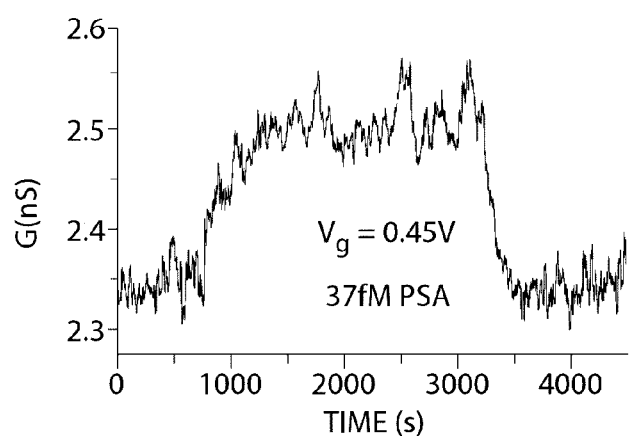
Figure 4F:
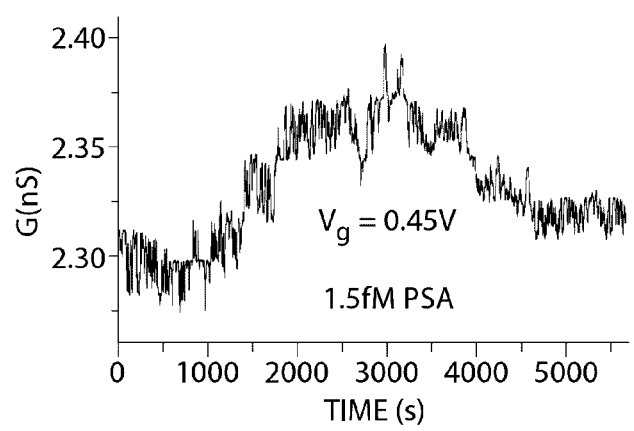

Additionally, concentration dependent detection was used to compare the PSA detection limits of the device in the linear vs. subthreshold regime. Real-time conductance sensing data are presented in FIGS. 4A-4B to show the detection limit ~0.75 pM for a NW sensor with $g_m=2800$ nS/V in the linear regime ($V_g=0$ V). The curves show a minimal PSA detection limit ~0.75 pM for this device in the linear regime. The same device had a subthreshold slope S=100 mV/decade in the subthreshold regime. FIGS. 4C-4F show the time dependent conductance measurements for detecting various PSA concentrations (15 pM, 0.75 pM, 37 fM and 1.5 fM) in the subthreshold regime of the same device. These data show that the detection limit of the device improved from ~0.75 pM in the linear regime to ~1.5 fM in the subthreshold regime. Therefore, with FIGS. 3 and 4, it can be seen that protein detection in the subthreshold regime of the NW sensor used here has not only a better signal to noise ratio, but a better detection limit.

Example 4

To calculate Δϕ(r), the potential profile inside a NW in responding to an adsorbed surface charge of σ (per unit length of NW), one solves the Poisson equation in cylindrical coordinates as:

$$\frac{1}{r}\frac{d}{dr}\left(r\frac{d(\Delta\varphi)}{dr}\right) = -\frac{e}{\varepsilon_{Si}}\Delta p \qquad (S1)$$

where change in the hole density in NW is $\Delta p(r)=p_i\times\exp[(E_i-e\Delta\phi-E_F)]/k_BT-p_i\times\exp(E_i-E_F)/k_BT=p\times[\exp(-e\Delta\phi)/k_BT-1]$.

For a small perturbation ($e\Delta\phi\ll k_BT$), Eq. S1 can be linearized to:

$$\frac{1}{r}\frac{d}{dr}\left(r\frac{d(\Delta\varphi)}{dr}\right) = \frac{pe^2\Delta\varphi}{\varepsilon_{Si}k_BT} = \frac{\Delta\varphi}{\lambda_{Si}^2}, \qquad (S2)$$

with $\lambda_{Si}=\sqrt{\varepsilon_{Si}k_BT/pe^2}$ being the Debye length in silicon with hole density p. The solution of Eq. S2 for boundary conditions $\Delta\phi(R)=\Delta\phi_{Si}$ and $\Delta\phi(0)=$finite is:

$$\Delta\phi(r)=\Delta\phi_{Si}\times I_0(r/\lambda_{Si})/I_0(R/\lambda_{Si}) \qquad (S3).$$

Here $I_0(x)$ is the zero-order modified Bessel function of the first kind and $\Delta\phi_{Si}$ is the potential at Si/SiO$_2$ interface. Eq. S3 is plotted in FIG. 5 at different $R/\lambda_{Si}$. It is important to note that for small $x=R/\lambda_{Si}\ll 1$, $I_0(x)\approx 1$, Eq. S3 physically means that for large $\lambda_{Si}$ and/or small R, surface charges gate the whole cross-section of NW. For large $$x = R/\lambda_{Si} \gg 1, I_0(x) \approx \frac{e^x}{\sqrt{2\pi x}},$$

and the potential falls off quasi-exponentially from the surface of NW within a layer of thickness $\sim\lambda_{Si}$. FIG. 5 shows the potential distribution $\Delta\phi(r)$ inside silicon nanowire at different ratios between the nanowire radius R and the carrier screening length $\lambda_{Si}$. $\Delta\phi(r)$ is normalized by its value at surface.

Following is a discussion of the relationship between surface charge and surface potential. Due to the total charge neutrality of the system:

$$\sigma = \qquad\qquad\qquad\qquad\qquad\qquad\qquad\qquad\qquad (S4)$$
$$-e \times \int_0^R 2\pi r \Delta p(r) dr = e \times \int_0^R 2\pi r \times p \times \{1 - \exp(-e\Delta\varphi/k_B T)\} dr.$$

Solving Eq. S3 and S4 gives how much the surface potential $\Delta\phi_{Si}$ is for surface charge adsorption of $\sigma$.

Now consider two limiting cases: $R \ll \lambda_{Si}$ (low carrier density) or $R \gg \lambda_{Si}$ (high carrier density). For $x = R/\lambda_{Si} \ll 1$, $I_0(x) = 1 + O(x^2) \approx 1$:

$$\Delta\phi(r) \approx \Delta\phi_{Si}$$

For $0 \leq r \leq R$; Eq. S4 simplifies to:

$$\sigma = e \times \pi R^2 \times p \times \{1 - \exp(-e\Delta\phi_{Si}/k_B T)\} \qquad (S5).$$

Note that although the Poisson equation S1 treats NW as a 3D system, the result of exponential dependence of $\sigma$ on $\Delta\phi_{Si}$ at $R \ll \lambda_{Si}$ will not change even if the radial confinement of NW is considered and the system is 1D. This is because, in Eq. S5, the carriers are thermally activated and follow Boltzmann statistics. For the 1D case, one replaces $\pi R^2 \times p$ in Eq. S5 with the 1D charge density per unit length. If a small perturbation is considered ($e\Delta\phi \ll k_B T$), Eq. 4 can be linearized and evaluated:

$$\sigma \approx e \times \int_0^R 2\pi r \times p \times e\Delta\varphi(r)/k_B T dr = \qquad (S6)$$
$$p \times 2\pi R \lambda_{Si} \times \frac{e^2 \Delta\varphi_{Si}}{k_B T} \times \frac{I_1(R/\lambda_{Si})}{I_0(R/\lambda_{Si})},$$

where $I_1(x)$ is the first-order modified Bessel function of the first kind, and the relationship $dxI_1(x)/dx = xI_0(x)$ is used. For $R/\lambda_{Si} \gg 1$, Eq. S6 further simplifies to:

$$\sigma \approx p \times 2\pi R \lambda_{Si} \times \frac{e^2 \Delta\varphi_{Si}}{k_B T}. \qquad (S7)$$

By differentiating Eq. S6, the differential capacitance of nanowire is:

$$C_{NW} = \frac{d\sigma}{d\Delta\varphi} \approx \frac{e^2 \times p \times \pi R^2}{k_B T} \times \frac{2\lambda_{Si}}{R} \times \frac{I_1(R/\lambda_{Si})}{I_0(R/\lambda_{Si})}. \qquad (S8)$$

Eq. S8 gives the charging capacitance of a NW and has the following asymptotic behavior: $C_{NW} \approx e^2 \times p \times 2\pi R \lambda_{Si}/k_B T$ for $\lambda_{Si} \ll R$; and $C_{NW} \approx e^2 \times p \times \pi R^2/k_B T$ for $\lambda_{Si} \gg R$. Note that Eq. S8 at the $\lambda_{Si} \gg R$ limit is consistent with the well known compressibility of a non-degenerate electron gas, and remains valid for 1D after replacing $p \times \pi R^2$ with the 1D charge density (which can be shown to be true by calculating the exact density dependence of the chemical potential of 1D Fermions at finite temperatures). The screening length of silicon enters $C_{NW}$ in the expression at the $\lambda_{Si} \ll R$ limit accounts for the fact that the chemical potential of carriers in NW only changes inside a layer of thickness $\sim \lambda_{Si}$ nearby its surface.

For the capacitance between an electrolyte solution and a nanowire, first, consider the potential distribution in the double layer (DL) formed by electrolyte near NW surface. The Poisson equation is:

$$\frac{1}{r}\frac{d}{dr}\left(r\frac{d\varphi}{dr}\right) = \qquad\qquad\qquad\qquad\qquad (S9)$$
$$-\frac{\rho e}{\varepsilon}\exp(-e\varphi/k_B T) + \frac{\rho e}{\varepsilon}\exp(e\varphi/k_B T) = \frac{2\rho e}{\varepsilon}\sinh(e\varphi/k_B T),$$

where $\rho$ and $\in$ are the ionic concentration and dielectric constant of the electrolyte. The solution of Eq. S9 for boundary conditions $\phi(R) = \Delta\phi$ and $\phi(\infty) = 0$ and small perturbations is:

$$\phi(r) = \Delta\phi \times K_0(r/\lambda)/K_0(R/\lambda), \text{ and } r \geq R \qquad (S10),$$

where $\lambda$ is the Debye-Huckel screening length of electrolyte and $K_0(x)$ is the zero-order modified Bessel function of the second kind, which has asymptotic behavior $K_0(x) \approx -\ln(x)$ for $x \ll 1$. Additionally, $$K_0(x) \approx \frac{e^{-x}}{\sqrt{2x/\pi}} \text{ for } x \gg 1.$$

The total charge inside the DL is:

$$Q = \int_R^\infty -\rho \times e \times 2\pi r \times \sinh(e\varphi/k_B T) dr \approx \qquad (S11)$$
$$\int_R^\infty -\rho \times e \times 2\pi r \times e\varphi(r)/k_B T dr =$$
$$-\frac{\rho e^2 2\pi R \lambda \Delta\varphi}{k_B T} \frac{K_1(R/\lambda)}{K_0(R/\lambda)} = -\pi \varepsilon \Delta\varphi \times \frac{R}{\lambda} \times \frac{K_1(R/\lambda)}{K_0(R/\lambda)}$$

This derivation makes use of the relationship $dxK_1(x)/dx = -xK_0(x)$ and $\lambda^2 = \in k_B T/2\rho e^2$. For an electrolyte with low ionic strength ($R/\lambda = x \ll 1$): $K_0(x) \sim -\ln(x)$ and $K_1(x) \sim 1/x$, Eq. S11 turns into $$Q = \frac{\pi \varepsilon \Delta\varphi}{\ln(R/\lambda)}.$$

Therefore the capacitance between solution and per unit length of NW is (denote as DL capacitance $C_{DL}$):

$$C_{DL} = |Q|/\Delta\varphi = \pi\varepsilon \times \frac{R}{\lambda} \times \frac{K_1(R/\lambda)}{K_0(R/\lambda)} \approx \frac{\pi\varepsilon}{\ln(\lambda/R)}; \text{ if } R \ll \lambda, \qquad (S12)$$

where the asymptotic behavior at small $R/\lambda$ is a logarithmic dependence, similar to the naïve picture of modeling DL as two cylindrical sheets of charges separated at distance of screening length: $2\pi\in/\ln(1+\lambda/R)$.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
    exposing a nanoscale wire, having a reaction entity immobilized relative thereto, to a solution suspected of containing an analyte that the reaction entity is able to bind,
    wherein the nanoscale wire has a Debye screening length, when the nanoscale wire is placed in the solution, that is greater than the average cross-sectional dimension of the nanoscale wire.

2. A method, comprising:
    exposing a nanoscale wire, having a reaction entity immobilized relative thereto, to a solution suspected of containing an analyte that the reaction entity is able to bind; and
    operating the nanoscale wire under conditions wherein the nanoscale wire has a conductance that is not linearly proportional to voltage applied to the nanoscale wire.

3. The method of claim 1 further comprising
    determining a change in charge of the analyte of less than about $10^{-17}$ coulombs.

4. The method of claim 3, wherein the change in charge of the analyte is less than about 20 electron charges.

5. The method of claim 3, wherein the change in charge of the analyte is less than about 10 electron charges.

6. The method of claim 1, wherein the reaction entity comprises a nucleic acid.

7. The method of claim 1, wherein the reaction entity comprises a protein.

8. The method of claim 1, wherein the reaction entity comprises an enzyme.

9. The method of claim 1, wherein the reaction entity comprises an antibody.

10. The method of claim 1, wherein the reaction entity is covalently immobilized to the nanoscale wire.

11. The method of claim 1, wherein the reaction entity is immobilized to the nanoscale wire via a linker.

12. The method of claim 1, wherein the reaction entity is positioned within 5 nanometers of the nanowire.

13. The method of claim 1, wherein the reaction entity is positioned within 3 nanometers of the nanowire.

14. The method of claim 1, wherein the reaction entity is positioned within 1 nanometer of the nanowire.

15. The method of claim 3, wherein the nanoscale wire is a semiconductor nanowire.

16. The method of claim 15, wherein the semiconductor nanowire is a silicon nanowire.

17. The method of claim 1, wherein the reaction entity specifically binds the analyte.

18. The method of claim 1, wherein the reaction entity nonspecifically binds the analyte.

19. The method of claim 3, wherein the nanoscale wire is contained in the solution.

20. The method of claim 1, wherein the solution has an ionic strength of less than about 10 millimolar.

\* \* \* \* \*